(12) United States Patent
Jalali et al.

(10) Patent No.: US 10,593,039 B2
(45) Date of Patent: Mar. 17, 2020

(54) DEEP LEARNING IN LABEL-FREE CELL CLASSIFICATION AND MACHINE VISION EXTRACTION OF PARTICLES

(71) Applicant: THE REGENTS OF THE UNIVERSITY OF CALIFORNIA, Oakland, CA (US)

(72) Inventors: Bahram Jalali, Los Angeles, CA (US); Ata Mahjoubfar, Los Angeles, CA (US); Lifan Chen, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/928,992

(22) Filed: Mar. 22, 2018

(65) Prior Publication Data

US 2018/0286038 A1 Oct. 4, 2018

Related U.S. Application Data

(63) Continuation of application No. PCT/US2016/053153, filed on Sep. 22, 2016.
(Continued)

(51) Int. Cl.
*G06K 9/00* (2006.01)
*G06T 7/00* (2017.01)
(Continued)

(52) U.S. Cl.
CPC ......... *G06T 7/0012* (2013.01); *G01N 15/147* (2013.01); *G01N 15/1429* (2013.01);
(Continued)

(58) Field of Classification Search
CPC .......... G06T 7/0012; G06N 3/086; G01N 2015/1445; G01N 15/1434; G01N 15/1475; G06F 19/24
See application file for complete search history.

(56) References Cited

U.S. PATENT DOCUMENTS

| | | | | |
|---|---|---|---|---|
| 5,862,304 A | * | 1/1999 | Ravdin | ............... G06N 3/0635 706/21 |
| 6,463,438 B1 | * | 10/2002 | Veltri | ................... G06K 9/0014 706/15 |

(Continued)

FOREIGN PATENT DOCUMENTS

| | | |
|---|---|---|
| WO | 2015021332 A1 | 2/2015 |
| WO | 2015069827 A2 | 5/2015 |

OTHER PUBLICATIONS

Korean Intellectual Property Office (KIPO), International Search Report and Written Opinion dated Jan. 13, 2017, related PCT international application No. PCT/US2016/053153, pp. 1-16, claims searched, pp. 17-23.

(Continued)

*Primary Examiner* — Amir Alavi
(74) *Attorney, Agent, or Firm* — O'Banion & Ritchey LLP; John P. O'Banion

(57) ABSTRACT

A method and apparatus for using deep learning in label-free cell classification and machine vision extraction of particles. A time stretch quantitative phase imaging (TS-QPI) system is described which provides high-throughput quantitative imaging, and utilizing photonic time stretching. In at least one embodiment, TS-QPI is integrated with deep learning to achieve record high accuracies in label-free cell classification. The system captures quantitative optical phase and intensity images and extracts multiple biophysical features of individual cells. These biophysical measurements form a hyperdimensional feature space in which supervised learn- (Continued)

ing is performed for cell classification. The system is particularly well suited for data-driven phenotypic diagnosis and improved understanding of heterogeneous gene expression in cells.

23 Claims, 16 Drawing Sheets

Related U.S. Application Data

(60) Provisional application No. 62/222,714, filed on Sep. 23, 2015, provisional application No. 62/222,720, filed on Sep. 23, 2015.

(51) Int. Cl.
  *G16B 40/00* (2019.01)
  *G06N 3/08* (2006.01)
  *G01N 15/14* (2006.01)
  *G06K 9/46* (2006.01)
  *G06N 3/04* (2006.01)
  *G01N 15/10* (2006.01)

(52) U.S. Cl.
  CPC ..... *G01N 15/1434* (2013.01); *G01N 15/1475* (2013.01); *G06K 9/0014* (2013.01); *G06K 9/00127* (2013.01); *G06K 9/00147* (2013.01); *G06K 9/4628* (2013.01); *G06N 3/04* (2013.01); *G06N 3/086* (2013.01); *G16B 40/00* (2019.02); *G01N 2015/1006* (2013.01); *G01N 2015/144* (2013.01); *G01N 2015/149* (2013.01); *G01N 2015/1445* (2013.01); *G01N 2015/1454* (2013.01)

(56) References Cited

U.S. PATENT DOCUMENTS

| | | | |
|---|---|---|---|
| 7,058,616 B1* | 6/2006 | Larder | G16B 40/00 706/15 |
| 8,140,300 B2* | 3/2012 | Dunne | G01N 15/1427 702/186 |
| 9,013,692 B2* | 4/2015 | Hu | G01N 15/147 250/459.1 |
| 9,934,364 B1* | 4/2018 | Kumar | G06N 3/0454 |
| 2005/0266395 A1 | 12/2005 | Gholap | |
| 2008/0082468 A1 | 4/2008 | Long | |
| 2018/0286038 A1* | 10/2018 | Jalali | G06N 3/04 |

OTHER PUBLICATIONS

Lau, Andy K. S. et al., "Interferomic time-stretch microscopy for ultrafast quantitative cellular and tissue imaging at 1um", Journal of Biomedical Optics, 2014, v. 19, n. 7, pp. 076001-1 to 076001-7, Jul. 2014.

Chen, Claire Lifen et al., "Deep Learning in Label-free Cell Classification", nature.com, Scientific Reports vol. 6, Article No. 21471 (2016), doi:10.1038/srep21471, pp. 1-16, supplementary methods, pp. 17-21, published Mar. 15, 2016.

* cited by examiner

24

68 — Frames — Pulse Synchronization
BB → [Pixels]

70 — Wavefronts — Phase Extraction

72 — $\lambda_1 t_1 | \lambda_1 t_2 | \lambda_1 t_3$ / $\lambda_2 t_1$ / $\lambda_3 t_1$ — Feature Extraction 74 — Machine Learning

FIG. 2C

DEEP LEARNING IN LABEL-FREE CELL CLASSIFICATION AND MACHINE VISION EXTRACTION OF PARTICLES

CROSS-REFERENCE TO RELATED APPLICATIONS

This application is a 35 U.S.C. § 111(a) continuation of PCT international application number PCT/US2016/053153 filed on Sep. 22, 2016, incorporated herein by reference in its entirety, which claims priority to, and the benefit of U.S. provisional patent application Ser. No. 62/222,714 filed on Sep. 23, 2015, incorporated herein by reference in its entirety, and which also claims priority to, and benefit of U.S. provisional patent application Ser. No. 62/222,720 filed on Sep. 23, 2015, incorporated herein by reference in its entirety. Priority is claimed to each of the foregoing applications.

The above-referenced PCT international application was published as PCT International Publication No. WO 2017/053592 on Mar. 30, 2017, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to label-free cell analysis, and more particularly to label-free cell classification with integrated feature extraction and deep learning.

2. Background Discussion

Flow cytometry is a powerful tool for large-scale cell analysis due to its ability to measure anisotropic elastic light scattering of millions of individual cells as well as emission of fluorescent labels conjugated to cells. However, each cell is represented with single values per detection channels (forward scatter, side scatter, and emission bands) and often requires labeling with specific biomarkers for acceptable classification accuracy. Imaging flow cytometry on the other hand captures images of cells, revealing significantly more information about the cells. For example, it can distinguish clusters and debris that would otherwise result in false positive identification in a conventional flow cytometer based on light scattering.

In addition to classification accuracy, the throughput is another critical specification of a flow cytometer. Indeed high throughput, typically 100,000 cells per second, is needed to screen a large enough cell population to find rare abnormal cells that are indicative of early stage diseases. However there is a fundamental trade-off between throughput and accuracy in any measurement system. For example, imaging flow cytometers are subject to a throughput limit imposed by the speed of the CCD or the CMOS cameras, a number that is approximately 2000 cells/s for present systems. Higher flow rates lead to blurred cell images due to the finite camera shutter speed. Many applications of flow analyzers such as cancer diagnostics, drug discovery, biofuel development, and emulsion characterization require classification of large sample sizes with a high-degree of statistical accuracy, thus spurring research into alternative optical diagnostic techniques for characterization of cells and particles in flow.

Accordingly, a need exists for a more accurate method of sorting flow cytometry particles. The present disclosure fulfills that need as well as others while overcoming trade-offs between sensitivity and image capture speeds.

BRIEF SUMMARY

A label-free imaging flow-cytometry technique based on coherent optical implementation of the photonic time stretch concept. This instrument overcomes the trade-off between sensitivity and speed by using an amplified time-stretch dispersive Fourier transform (TS-DFT). A time stretch quantitative phase imaging (TS-QPI) system is disclosed in which the spatial information from the object is encoded in the spectrum of laser pulses within a pulse duration of sub-nanoseconds (see FIG. 1 and FIG. 2A through FIG. 2B). Each pulse representing one frame of the camera is then stretched in time so that it can be digitized in real-time by an electronic analog-to-digital converter (ADC). The ultra-fast pulse illumination freezes the motion of high-speed cells or particles in flow to achieve blur-free imaging. Detection sensitivity is challenged by the low number of photons collected during the ultra-short shutter time (optical pulse width) and the drop in peak optical power resulting from the time stretch. These issues are solved in time stretch imaging by implementing a low noise-figure Raman amplifier within the dispersive device that performs time stretching. Moreover, a warped stretch transform is utilized in the disclosed time stretch imaging to achieve optical image compression and non-uniform spatial resolution over the field-of-view (FOV). In the coherent version of the instrument, the time stretch imaging is combined with spectral interferometry to measure quantitative phase and intensity images in real-time and at high throughput.

Integrated with a microfluidic channel, coherent time stretch imaging system in this work measures both quantitative optical phase shift and loss of individual cells as a high-speed imaging flow cytometer, for example able to capture 36 million images per second in flow rates as high as 10 meters per second, reaching up to 100,000 cells per second throughput.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 2A through FIG. 2C are detailed block diagrams of the time stretch quantitative phase imaging (TS-QPI) system shown in FIG. 1 according to an embodiment of the present disclosure.

DETAILED DESCRIPTION

1. Introduction

Deep learning extracts patterns and knowledge from rich multi-dimensional datasets. While the deep learning paradigm is used extensively for image recognition and speech processing, its application to label-free classification of cells has not been exploited. The present disclosure illustrates a method and apparatus which benefits from deep learning.

2. Time Stretch Quantitative Phase Imaging

Figure 1:
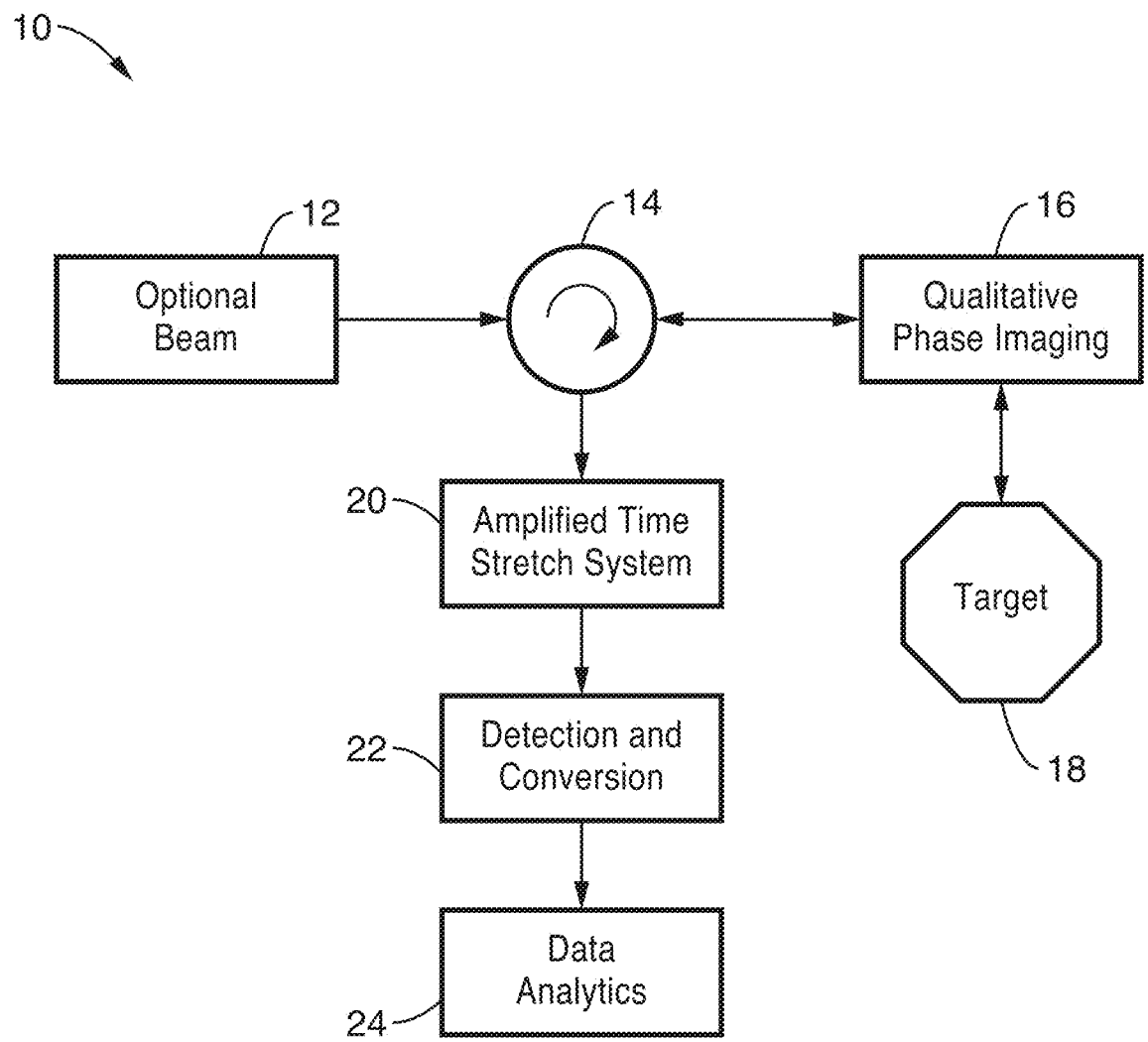
FIG. 1 is a block diagram of a time stretch quantitative phase imaging (TS-QPI) system according to an embodiment of the present disclosure.

FIG. 1 illustrates an example embodiment 10 of a time stretch quantitative phase imaging (TS-QPI) and analytics system. The system generally comprises an optical beam system 12 coupled to an optical circulator 14, which is coupled to a qualitative phase imaging system 16 for interacting with target 18. Output from qualitative phase imaging system 16 is received at the optical circulator 14 and directed to an amplified time stretch module 20, with output to a detection and conversion module 22, which is coupled to a data analytics module 24. The following figure explains these elements with increased particularity.

Figure 2A:
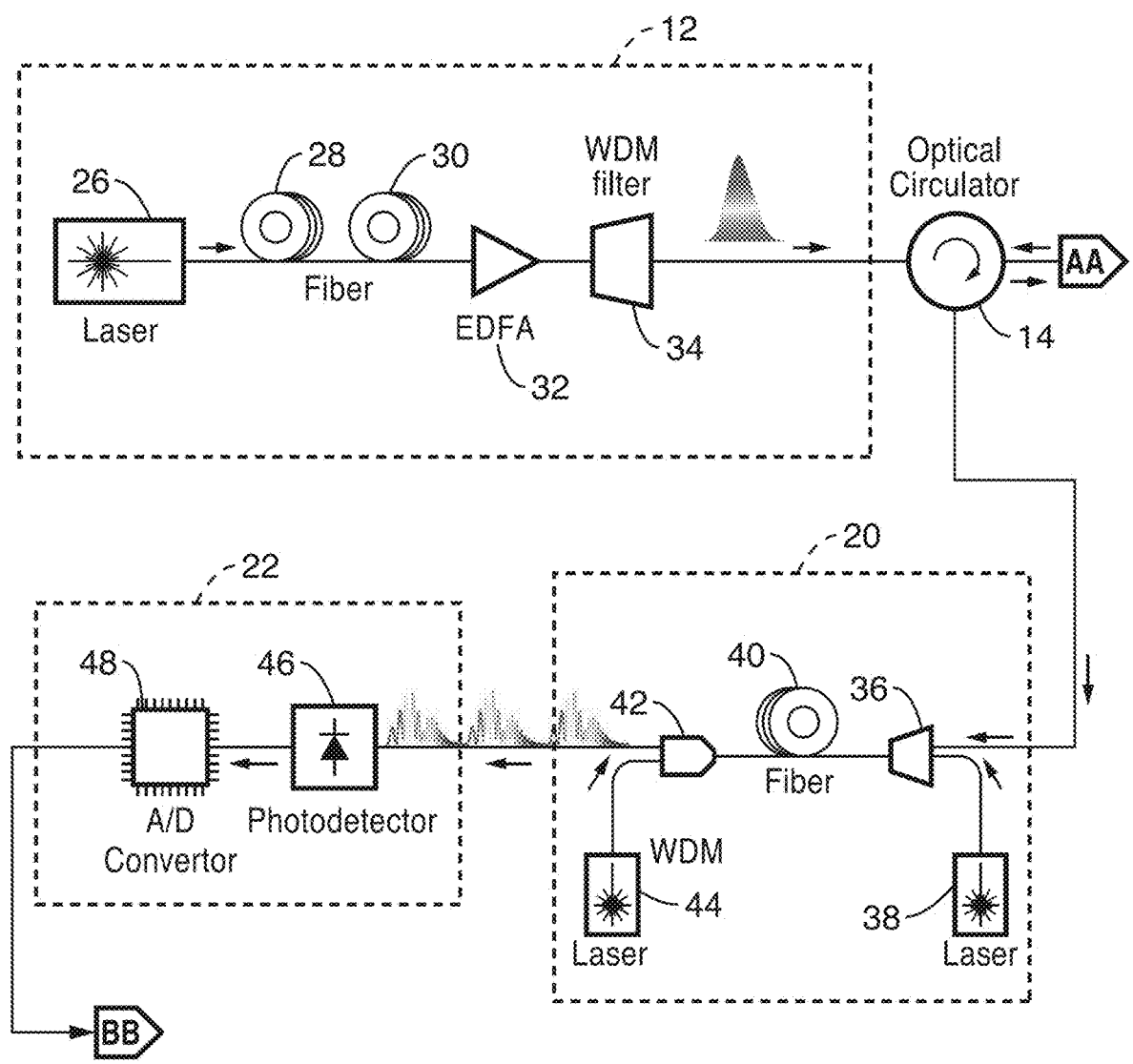
Figure 2B:
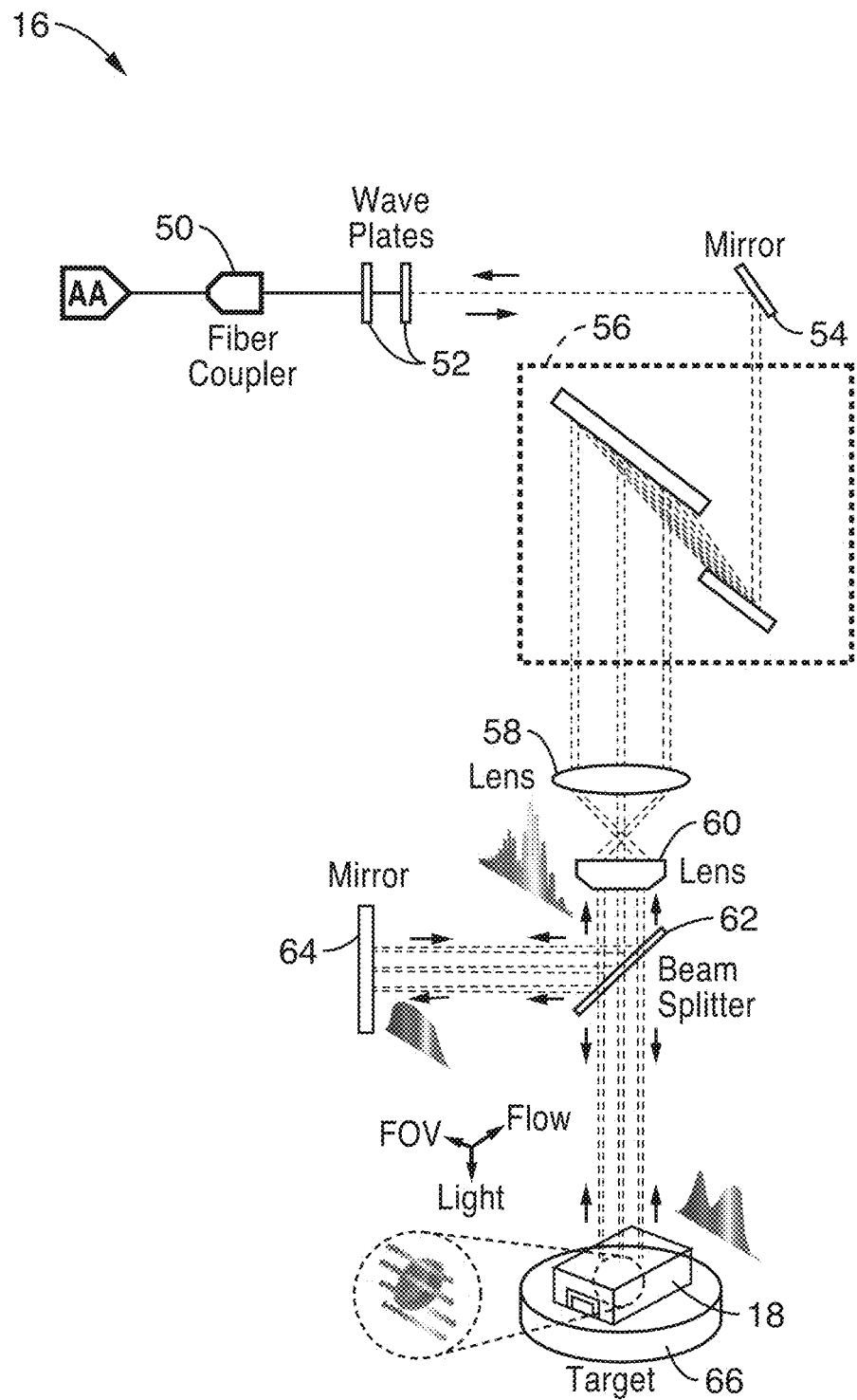

FIG. 2A through FIG. 2C illustrate the time stretch quantitative phase imaging (TS-QPI) and analytics system separated into three figures to show additional details.

In FIG. 2A is seen optical beam system 12, coupled to an optical circulator 14, with output from the optical circulator coupled to an amplified time stretch system 20, then to detection and conversion module 22. By way of example and not limitation, the optical beam system is depicted with a mode-locked laser 26 followed by a nonlinear fiber 28, a dispersion compensating fiber 30, an erbium doped fiber amplifier (EDFA) 32, followed by a wavelength-division multiplexing (WDM) filter 34 which generates and shapes a train of broadband optical pulses directed into optical circulator 14.

In FIG. 2B is seen quantitative phase imaging 16 directed at target 18. The pulse train from optical beam system 12 through optical circulator 14 of FIG. 2A is received at coupler 50 which outputs light to wave plates 52 to a mirror 54 to diffraction gratings 56, coupled to a spherical lens 58 directed to an objective lens 60. Output from objective lens 60 is directed to a beam splitter 62, to/from target 18 and mirror 64 forming the reference arm of the interferometer. In the example, target 18 is shown on a stage 66, or other structure as desired.

The light pulses of the input pulse train are thus spatially dispersed into a train of rainbow flashes illuminating the target as line scans. The spatial features of the target are encoded into the spectrum of the broadband optical pulses, each representing a one-dimensional frame. The ultra-short optical pulse illumination freezes the motion of cells during high speed flow to achieve blur-free imaging with a throughput of 100,000 cells/second. The phase shift and intensity loss at each location within the field of view (FOV) it thus embedded into the spectral interference patterns using this Michelson interferometer.

These patterns are directed back through the diffraction gratings and back to the optical circulator 14 to the amplified time-stretch system 20 in FIG. 2A. In the time stretching system a first WDM 36 receives a first input from optical circulator 14 and a second input from a Raman pump laser 38. Output from first WDM 36 is coupled to a dispersion compensating fiber 40 and received at a second WDM 42 which performs the converse of first WDM 36. Second WDM 42 is coupled to a Raman pump laser 44 and outputs pixel waveform patterns to detection and conversion module 22. The interferogram pulses are stretched in time in module 20 so that spatial information is mapped into time through time-stretch dispersive Fourier transform (TS-DFT), allowing them to be captured by a detection and conversion module 22 exemplified as comprising single pixel photodetector 46 and an analog-to-digital converter (ADC) 48. The loss of sensitivity at high shutter speed is compensated by stimulated Raman amplification during time stretch.

In FIG. 2C data analytics 24 are performed on the digitized waveform. In block 68 pulse synchronization is performed in which the time-domain signal carrying serially captured rainbow pulses is transformed into a series of one-dimensional spatial maps, which are used for forming line images. Then in block 70 biomass density of a cell leads to a spatially varying optical phase shift. When a rainbow flash passes through the cells, the changes in refractive index at different locations will cause phase walk-off at interrogation wavelengths. Hilbert transformation and phase unwrapping are used to extract the spatial phase shift. In block 72 feature extraction is performed by decoding phase shift in each pulse at each wavelength and remapping it into a pixel to reveal the protein concentration distribution within cells. The optical loss induced by the cells, embedded in the pulse intensity variations, is obtained from the amplitude of the slowly varying envelope of the spectral interferograms. Thus, quantitative optical phase shift and intensity loss images are captured simultaneously. Both images are calibrated based on the regions where the cells are absent. Cell features describing morphology, granularity, biomass, and so forth are extracted from the images. In block 74 these biophysical features are utilized in a machine learning algorithm for high-accuracy label-free classification of the cells.

It should be appreciated that surface markers used to label cells, such as EpCAM, are unavailable in some applications; for example, melanoma or pancreatic circulating tumor cells (CTCs) as well as some cancer stem cells are EpCAM-negative and will escape EpCAM-based detection platforms. Furthermore, large-population cell sorting are often precursors to operations performed downstream in which the negative impact of labels on cellular behavior and viability are often unacceptable. Cell labels may cause activating/inhibitory signal transduction, altering the behavior of the desired cellular subtypes, potentially leading to errors in downstream analysis, such as DNA sequencing and subpopulation regrowth. In this way, quantitative phase imaging (QPI) methods that categorize unlabeled living cells with high accuracy are needed. Coherent time stretch imaging is a method that enables quantitative phase imaging at ultrahigh throughput for non-invasive label-free screening of large numbers of cells.

In the present disclosure the information of quantitative optical loss and phase images are fused into expert designed features, leading to a record label-free classification accuracy when combined with deep learning. Image mining techniques are applied, for the first time, to time stretch quantitative phase imaging to measure biophysical attributes including protein concentration, optical loss, and morphological features of single cells at an ultrahigh flow rate and in a label-free fashion. These attributes differ widely among cells and their variations reflect important information of genotypes and physiological stimuli. The multiplexed biophysical features thus lead to information-rich hyper-dimensional representation of the cells for label-free classification with high statistical precision.

The present disclosure also provides improved accuracy, repeatability, and balance between sensitivity and specificity of label-free cell classification by a novel machine learning pipeline, which harnesses the advantages of multivariate supervised learning, as well as unique training by evolutionary global optimization of receiver operating characteristics (ROC). To demonstrate sensitivity, specificity, and accuracy of multi-feature label-free flow cytometry, the present disclosure was utilized to classify (1) OT-II hybridoma T-lymphocytes and SW-480 colon cancer epithelial cells, and (2) *Chlamydomonas reinhardtii* algal cells (herein referred to as *Chlamydomonas*) based on their lipid content, which is related to the yield in biofuel production. The preliminary results from these tests indicated that compared to classification by individual biophysical parameters, the disclosed label-free hyperdimensional technique improves the detection accuracy from 77.8% to 95.5%, or in other words, reduces classification inaccuracy by about a factor of five.

2.1 Results of Time Stretch Quantitative Phase Imaging

The application of time stretch quantitative phase imaging (TS-QPI) to imaging flow cytometry, as recently demonstrated in our group, is described below. Broadband optical pulses from a mode-locked laser were firstly conditioned in fiber optics and then spatially dispersed in free-space optics with a pair of reflection diffraction gratings creating 1-D "rainbow flashes" (refer to FIG. 2A through FIG. 2C). Each of the rainbow flashes was composed of all the wavelength components distributed laterally over the field of view. These flashes illuminated the target as in traditional photography, but in addition, rainbow flashes targeted different spatial points with distinct colors of light, resulting in space-to-spectrum encoding. Rainbow pulses were then split into the two arms of a Michelson interferometer. Different wavelength components of the rainbow flash traveled parallel to each other but individually focused on the mirror in the reference arm or on the reflective substrate of a microfluidic device in the sample arm. In the sample arm, the cells in the microfluidic channel were hydrodynamically focused into the field of view of the rainbow and flowed perpendicular to the rainbow flash. Reflected pulses from the microfluidic device and the reference arm were recombined and coupled back into the fiber, optically amplified and linearly chirped through Raman-amplified time-stretch dispersive Fourier transform (TS-DFT) system.

An amplified time-stretch system that utilizes a low-noise distributed Raman amplifier within dispersive fiber with a net optical gain of approximately 15 dB enables high-sensitivity detection at high speeds. An ultrafast single-pixel photodetector transformed instantaneous optical power into an electrical signal and subsequently, an analog-to-digital converter (ADC) samples and quantizes the signal. Acquired data are passed down to processing stages for 'big data analytics'. It should be appreciated that the term 'big data analytics' is generally considered to be the process of examining large data sets to uncover hidden patterns, unknown correlations, and mining of other useful information. The interference between time-shifted linearly chirped pulses create a beat (fringe) frequency, which can be adjusted via the interferometer arm length mismatch. Details of the demonstration system can be found in a later section of methods descriptions.

The photodetected time-stretched pulses, each representing one line scan, are converted to analytic signals using Hilbert transformation and the intensity and phase components are extracted. The phase component is a fast oscillating fringe (carrier frequency), caused by the interference of the linearly chirped pulses arriving from the reference and sample arms in the Michelson interferometer. Acting as a radio-frequency (RF) carrier whose frequency is set by the user adjusted arm length mismatch, the fringe frequency is modulated when the optical path length in the sample arm is changed by the arrival of a cell. This frequency shift and the accompanying phase change are used to measure the optical path length of the cell (see method: Coherent Detection and Phase Extraction). Since the phase varies over a wide range (much larger than $2\pi$ radians), an unwrapping algorithm is used to obtain the continuous phase profile. The phase profile contains the phase shift induced by the cell and an increasing term with time, corresponding to the fringe (beat) frequency. By eliminating the background phase component, the cell-induced phase shift is extracted. The second component in the waveform is a lower frequency envelope corresponding to temporal shape of the optical pulse. The amplitude of this envelope provides information about optical loss caused by transparency, surface roughness, and inner organelle complexity (see later section on Cell Transmittance Extraction).

2.2 Feature Extraction

Figure 3A:
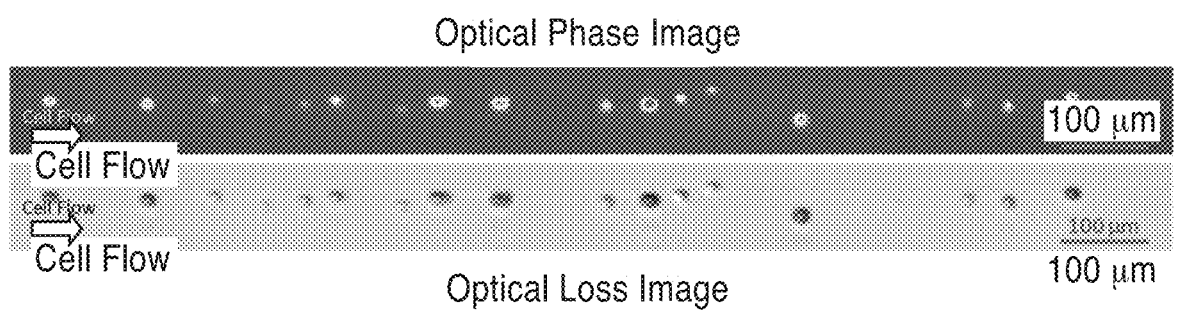
FIG. 3A and FIG. 3B are optical phase and optical loss images for a white blood cell line (OT-11) in FIG. 3A and a colon cancer cell line (SW-480) in FIG. 3B, captured according to an embodiment of the present disclosure.
Figure 3B:
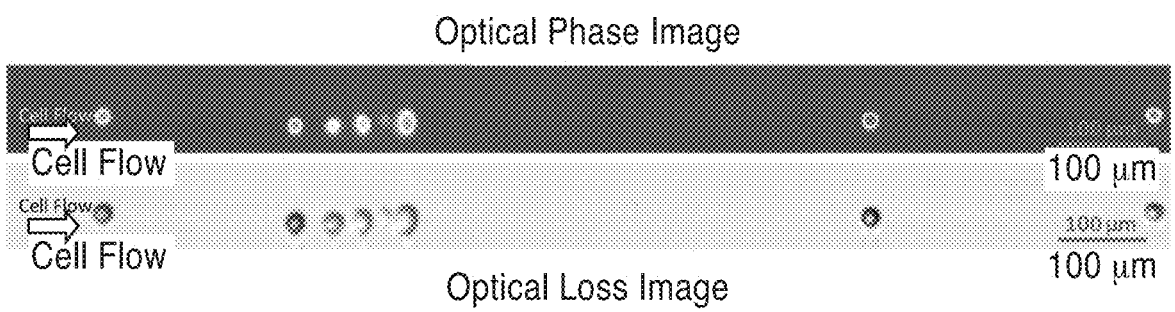

FIG. 3A and FIG. 3B illustrate optical phase and optical loss images for a white blood cell line (OT-11) in FIG. 3A and a colon cancer cell line (SW-480) in FIG. 3B. For each figure the optical phase image is shown across the top, under which is the optical loss image. The scale on these images is shown with a bar at the left side of each showing 100 µm. The decomposed components of sequential line scans form pairs of spatial maps, namely, optical phase and loss images as created according to the description herein of Image Reconstruction. These images are utilized to obtain biophysical fingerprints of the cells. With domain expertise, raw images are fused and transformed into a suitable set of biophysical features, as described below, which the deep learning model further converts into learned features for improved classification.

2.2.1 Feature List and Description per Category

Following is a list of the selected features and their description for each of the categories: morphological, optical phase, and optical Loss. The first portion of the features listed below are morphological.

Diameter-RB: Diameter along the interrogation rainbow. It is insensitive to flow rate fluctuation. For higher accuracy, it is calibrated by the spatial non-uniform distribution of rainbow wavelengths.

Diameter-FL: Diameter along the flow direction. It is sensitive to flow rate fluctuation, but can be a candidate parameter for monitoring flow speed and channel condition.

Tight Area: Total number of pixels in the segmented region in the phase image.

Perimeter: Total number of pixels around the boundary of each segmented region.

Circularity: $4\pi$(Tight Area)/Perimeter.

Major Axis: Considering the cell as elliptical in lateral imaging plane, the length of the major axis of the ellipse with a normalized second central moment same as the cell.

Orientation: Angle between the flow direction and the major axis of the cell elliptical shape.

Loose Area: Total number of pixels in the expanded segmented region for measurement of the pixel intensities.

Median Radius: The median distance of any pixel in the object to the closest pixel outside of the object.

The next group of features are in regard to Optical Phase.

OPD-1: Integrated optical path length difference within the entire segmented area (cell), calibrated by the power distribution within different wavelength components of the incident laser pulses.

OPD-2: Integrated optical path length difference within the entire segmented area (cell). In addition to the calibration of OPD-1, it is calibrated by the pulse-to-pulse fluctuations within a 1 µs detection window.

Refractive index: The mean refractive index difference between the object and the surrounding liquid (buffer solution), which is calculated based on OPD-2 and size measurement (see detail in Section Methods). Refractive index difference for cells is proportional to their protein concentration.

The next group of features are in regard to Optical Loss.

Absorption-1: Mean absorption coefficient within the entire segmented area (cell). It is calibrated by the power distribution within different wavelength components of the incident laser pulses and by the pulse-to-pulse fluctuations within a 1 µs detection window. This parameter corresponds to an absorption dominant model for the cell.

Absorption-2: Mean absolute absorption coefficient within the entire segmented area (cell). It is calibrated by the power distribution within different wavelength components of the incident laser pulses and by the pulse-to-pulse fluctuations within a 1 µs detection window. This parameter corresponds to an absorption-dominant model for the cell.

Scattering-1: Mean optical loss within the entire segmented area (cell). It is calibrated by the power distribution within different wavelength components of the incident laser pulses and by the pulse-to-pulse fluctuations within a 1 detection window. This parameter corresponds to a scattering-dominant model for the cell.

Scattering-2: Mean absolute optical loss within the entire segmented area (cell). It is calibrated by the power distribution within different wavelength components of the incident laser pulses and by the pulse-to-pulse fluctuations within a 1 µs detection window. This parameter corresponds to a scattering dominant model for the cell.

2.2.2 Optical Phase and Optical Loss Feature Imaging

The optical loss images of the cells, such as seen in FIG. 3A and FIG. 3B, are affected by the attenuation of multiplexed wavelength components passing through the cells. The attenuation itself is governed by the absorption of the light in cells as well as the scattering from the surface of the cells and from the internal cell organelles. The optical loss image is derived from the low frequency component of the pulse interferograms. The optical phase image is extracted from the analytic form of the high frequency component of the pulse interferograms using Hilbert Transformation, followed by a phase unwrapping algorithm. Details of these derivations are described in a later section.

The feature extraction operates on optical phase and loss images simultaneously, including object detection, segmentation, and feature measurement, as well as clump identification, noise suppression, and so forth. As an example of the expert designed features, the average refractive index, used as a measure of protein concentration, is obtained by dividing the integral of the optical path length by the cell volume. Since cells in suspension relax to a spherical shape (due to surface tension), an independent measure of cell diameter can be obtained from its lateral dimension for volume estimation.

In feature extraction, one of the most important advantages of optical loss and phase fusion, is its robustness and insensitivity to axial defocusing caused by the limited depth-of-focus of the objective lens and variations of the cell alignment in microfluidic channel. Diffracted photons have little chance to be influential in phase images. This makes the size measurements in optical phase images relatively accurate and consistent, more suitable than direct size measurements in optical loss images for extraction of scattering and absorption features. Among different features, size measurement is particularly important as it is used by itself in many technologies.

2.2.3 Statistical Characteristics Obtained from TS-QPI

The large data set captured by TS-QPI provides sufficient statistical characteristics for performing cell analysis based on biophysical features. Since cells from even the same line or tissue exhibit variations in size, structure, and protein expression levels, high accuracy classification can only be achieved by a model tolerant to these intrinsic variations. On the other hand, the feature extractor must reflect the intricate and tangled characteristics caused by extrinsic variations, for example in drug treatment, cell cycles, rare cell types, labeling, and transcription rate.

A total of sixteen features are chosen (although a different number or selection can be used without departing from the invention) among the features extracted from fusion of optical phase and loss images of each cell. Features that are highly correlated do not provide unique information.

Figure 4A:
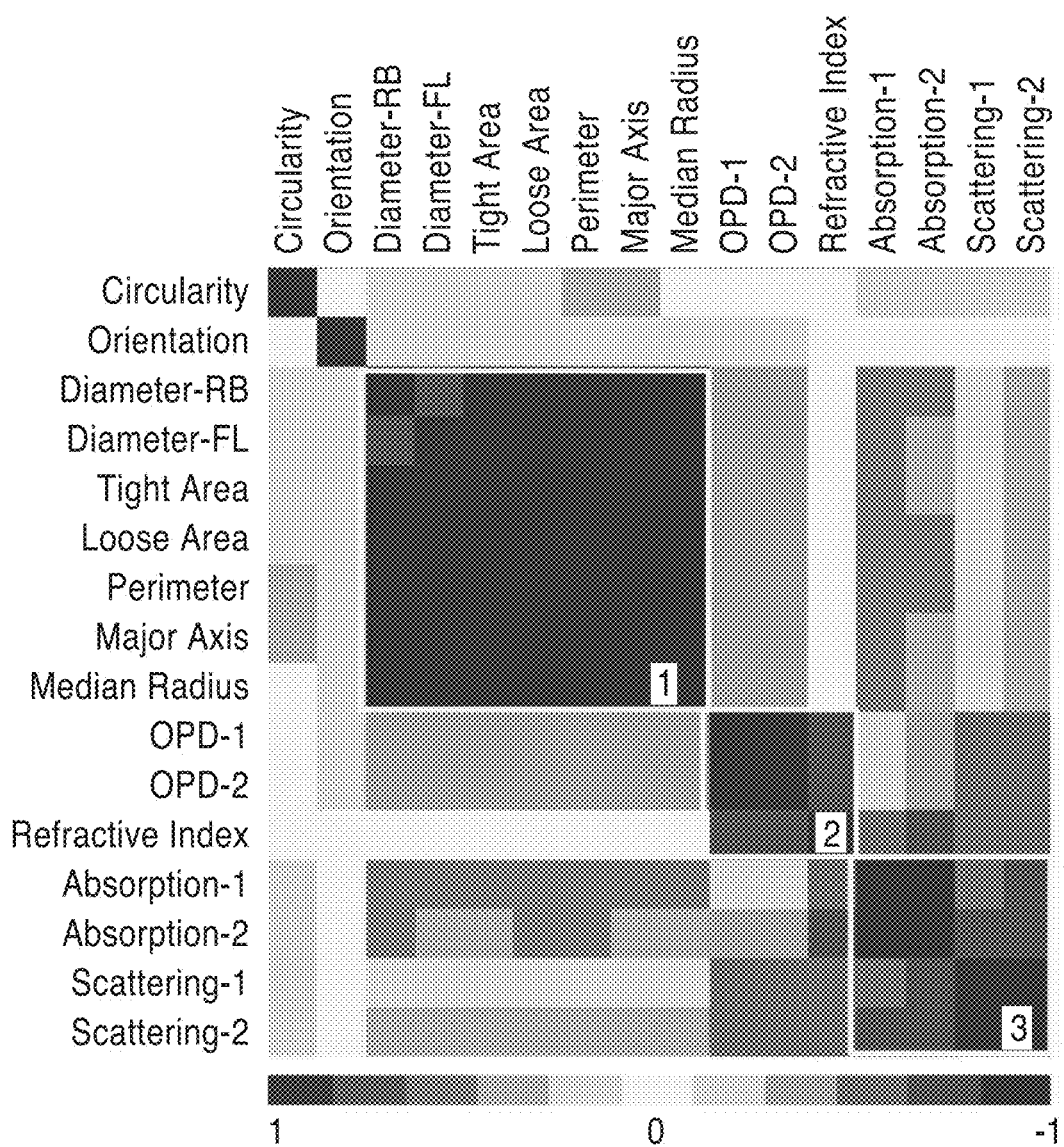
FIG. 4A and FIG. 4B are a heat map of pairwise correlation and a ranking, respectively, of sixteen biophysical features according to an embodiment of the present disclosure.
Figure 4B:
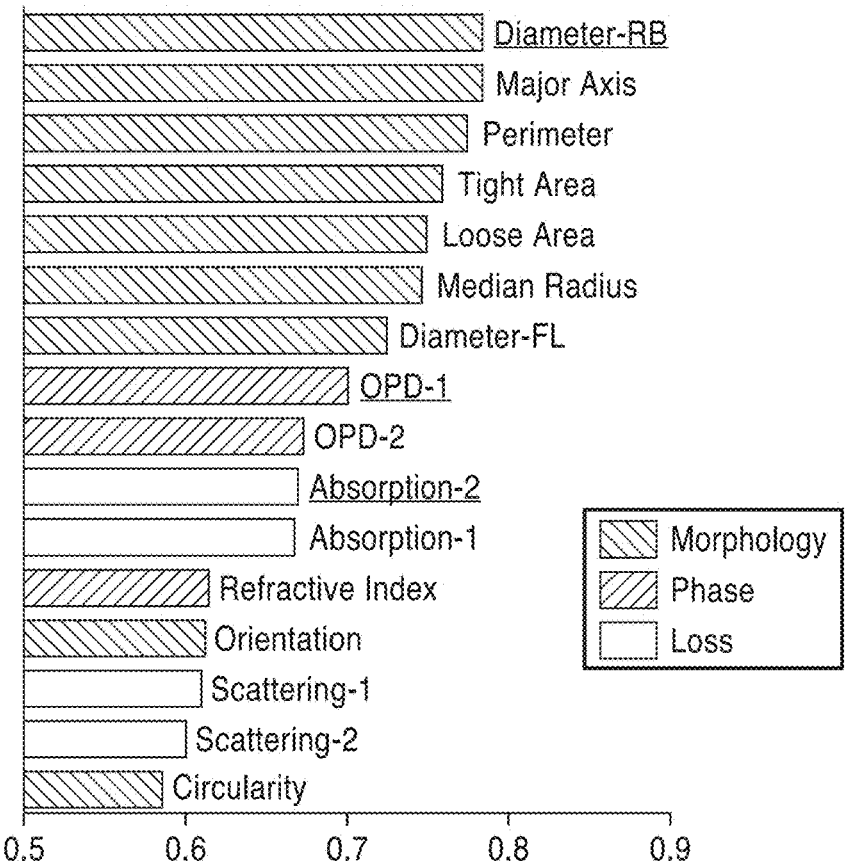

FIG. 4A and FIG. 4B illustrate a heat map of the pairwise correlation matrix among these features in FIG. 4A, and with a ranking of sixteen biophysical features based on their area-under-curve (AUC) in single-feature classification as seen in FIG. 4B. One of ordinary skill in the art will recognize that a 'heat map', or 'heatmap', is a graphical representation of data (2D/3D) in which individual values are represented as colors. Colors are not seen in these images due to the limitations of the patent application process.

In regards to FIG. 4A, the diagonal elements of the matrix indicate a correlation of each feature with itself, that is to say an autocorrelation. In this figure there is a box toward the upper left marked as box "1", then a box "2" and box "3" are shown on the diagonal from box "1". The subset of features in box 1 indicates high correlation among morphological features. Also, the subset of features in box 2 and box 3 are correlated as they are mainly related to optical phase shift and optical loss, respectively.

The bars in FIG. 4B show performance of the listed morphological parameters, arranged by classification accuracy based on each single feature arranged in descending order, which includes diameter along the interrogation rainbow, tight cell area, loose cell area, perimeter, major axis length, median radius, diameter along the flow direction, orientation, and circularity. As expected, morphology parameters contain the bulk of the information, but other biophysical features can contribute to improved performance of label-free cell classification. Another group of bars show optical phase shift features, including optical path length differences (OPD-1, OPD-2) and refractive index differences. While another group of bars indicate optical loss features representing absorption (Absorption-2, Absorption-1) and scattering (Scattering-1, Scattering-2) by the cell. The best performing features (depicted as Diameter-RB, OPD-1, and Absorption-2) in this list are underlined.

The features are coded (e.g., color coded in the original image) into three categories: morphology, optical phase, and optical loss, to describe the main type of information provided by each. The figure provides valuable insight into the relative importance of each category of cell features and suggests that morphological features carry the most information about cells, but at the same time, significant additional information is contained in optical phase and loss measurements.

2.3 Machine Learning

Figure 5:
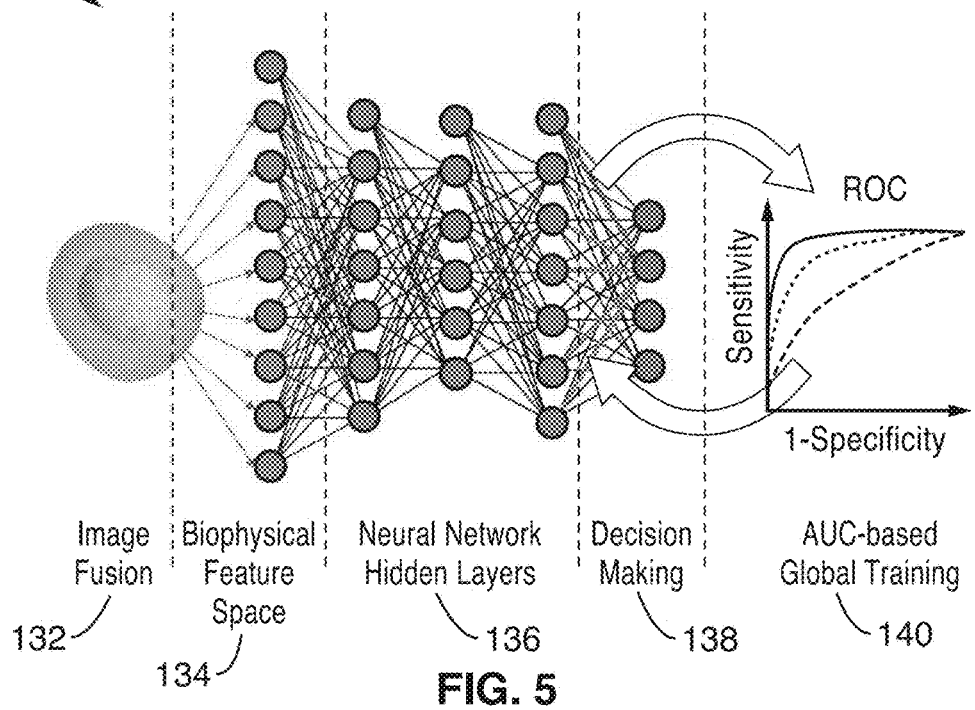
FIG. 5 is a neural stage diagram of a machine learning pipeline implemented as a neural network as utilized according to an embodiment of the present disclosure.

FIG. 5 illustrates an example machine learning pipeline embodiment 130 as a neural network. The neural network maps input features by a chain of weighted sum and nonlinear activation functions into learned feature space, as convenient for classification. This deep neural network (DNN) is globally trained utilizing area under the curve (AUC) of the receiver operating characteristics (ROC). Each ROC curve corresponds to a set of weights for connections to an output node, generated by scanning the weight of the bias node. The training process maximizes AUC, pushing the ROC curve toward the upper left corner, which equates to improved sensitivity and specificity in classification.

Information of quantitative optical phase and loss images are fused 132 to extract multivariate biophysical features of each cell, which are fed into a fully-connected neural network. In this figure an image fusion 132 is mapped into a first neural net layer of biophysical feature space 134, which is coupled to multiple hidden layers 136, followed by a decision making layer 138 interoperating with AUC-based global training 140.

It will be appreciated that neural networks are a flexible and powerful bioinspired learning model, which perform layers of nonlinear feature transformations, learned from the training data. The transformations morph the input data with weighted sums and nonlinear activation functions into feature spaces more suitable for classification. The unique feedforward neural network learning model as seen in the figure is globally trained by the objective of improving receiver operating characteristic (ROC). The learning algorithm introduced here maximizes the area under ROC curve (AUC), which is a global indicator of the classifier performance on the entire training dataset. The global training of the neural network, although computationally costly, results in a classifier more robust, repeatable, and insensitive to imbalance among classes. For the purpose of end-to-end supervised learning with AUC whose gradient is not well-behaved, a heuristic genetic algorithm (GA) is employed by way of example and not limitation, which is resilient to discontinuities of the cost function and being trapped in local minima during optimization.

The neural network maps input features by a chain of weighted sum and nonlinear activation functions into learned feature space, convenient for classification. This deep neural network is globally trained via area under the curve (AUC) of the receiver operating characteristics (ROC). Each ROC curve corresponds to a set of weights for connections to an output node, generated by scanning the weight of the bias node. The training process maximizes AUC, pushing the ROC curve toward the upper left corner, thus providing improved sensitivity and specificity in classification.

The network is composed of multiple hidden layers, which automatically learn representations of the data at different levels of abstraction, and thus, is considered a form of deep learning. Each layer performs a linear combination on its inputs from the previous layer and operates a nonlinear function on the weighted sums. The output of the node j in layer l+1, denoted by $z_j^{(l+1)}$ is generated from inputs $x_1^{(l)}$, $x_2^{(l)}, \ldots, x_N^{(l)}$ as:

$$z_j^{(l+1)} = h(a_j^{(l+1)}) = h\left(\sum_{i=0}^{N_l} \omega_{ji}^{(l)} x_i^{(l)}\right)$$

$$l = 0, \ldots, L; j = 1, \ldots, N_{l+1}$$

here $a_j^{(l+1)}$ is the linear combination of inputs, and $\omega_{ji}^{(l)}$ are the weights of the linear combination. The summation runs over $N_l$, the total number of nodes in the layer l, and L is the total number of hidden layers. $x_0^{(l)}$ is the bias node in layer l, whose value is conventionally 1. Some popular choices for the nonlinear activation function h(•) include logistic sigmoid function h(a)=1/(1+exp(−a)), hyperbolic tangent function tan h(a), and as commonly used in deep learning, rectified linear unit (ReLU) h(a)=max(0, a). In the exemplified learning model, ReLU is utilized, which typically speeds up the supervised learning process of deep neural network by inducing sparsity and preventing gradient vanishing problems. The only exception is the output node, where the logistic sigmoid function is utilized as the activation function. The deep neural networks DNNs in these tests are described by way of example and not limitation as having three hidden layers with 48 ReLUs in each, but the DNNs may be configured with differing numbers of layers and ReLUs in each. In addition, the present disclosure is not limited to use of the specific functions described above and throughout the disclosure, such as non-linear activation function, sigmoid function, ReLU, and so forth, as one of ordinary skill in the art will appreciate that alternatives can be applied without departing from the teachings herein.

For a trained classifier in hyperspace, receiver operating characteristics (ROC) curve describes the sensitivity and specificity of a classifier collection that includes nonlinear classifiers scaled in the direction of their normal vector field. In a deep learning network, this is equivalent to shifting the weight of the bias node in the last hidden layer. ROC highlights the trade-off between sensitivity and specificity (seen in FIG. 5), and the area under ROC (AUC) provides a quantitative robust measure of classifier performance. Choosing a large value for the weight of the bias node results in high sensitivity, but this sacrifices the specificity, leading to a large number of false positives. As a way to visualize the impact of the threshold on classification accuracy, a classifier that accurately separates the classes will have an ROC curve that approaches the upper left corner. Conversely, a random guess, corresponding to balanced accuracy of 50% in binary classification will have an ROC that appears as a diagonal line. The AUC parameter serves as an effective analysis metric for finding the best classifier collection and has been proven to be advantageous over the mean square error for evaluating learning algorithms.

To prevent overfitting in the deep learning model, a regularization term has been added to the AUC-based cost function. This regularization term is defined as a mean square of all the network weights, excluding the weight of the bias nodes. Therefore, the overall cost function, $cost(\omega)$, that is minimized by the genetic algorithm is $$cost(\omega) = (1 - AUC(\omega)) + \lambda \frac{\sum_{l=0}^{L} \sum_{j=1}^{N_{l+1}} \sum_{i=1}^{N_l} (\omega_{ji}^{(l)})^2}{\sum_{l=0}^{L} \sum_{j=1}^{N_{l+1}} \sum_{i=1}^{N_l} 1} \quad (2)$$

where $\lambda$ is the regularization parameter, which controls the trade-off between overfitting (variance) and underfitting (bias).

2.4 Demonstration in Classification of Cancerous Cells

In comparison with single-feature approaches, the label-free cell classification enabled by TS-QPI and multivariate analysis, offers considerable improvements in detection sensitivity and accuracy for cancer diagnosis. To demonstrate the application in circulating tumor cell (CTC) detection, OT-II hybridoma T cells were utilized as a model for normal white blood cells and SW-480 epithelial colon cancer cells. The features previously described were measured by the disclosed TS-QPI system for the aforementioned cells.

Figure 6:
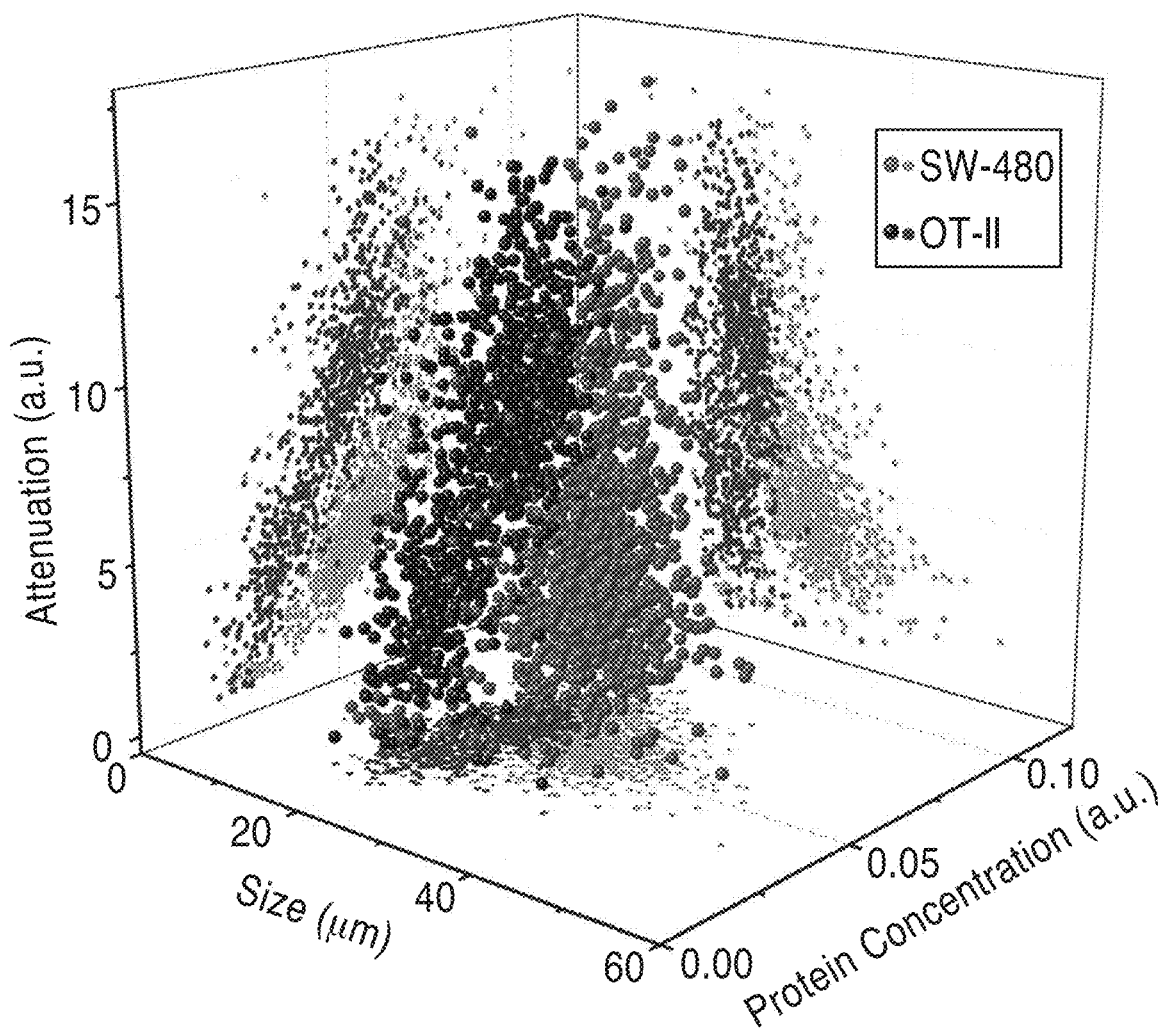
FIG. 6 is a 3D scatter plot of three features for OT-II and SW-480 models plotted in relation to size, protein concentration, and attenuation according to an embodiment of the presently disclosed time stretch quantitative phase imaging (TS-QPI) system.

FIG. 6 illustrates three of the previously described features for OT-II and SW-480 models, in a three-dimensional (3D) scatter plot, attributed to size, protein concentration, and attenuation, determined from TS-QPI. The 2D projections on the three orthogonal planes are also shown. The cell diameter along the rainbow (Diameter-RB) is used as a size indicator, while the cell protein concentration corresponds to the mean refractive index difference of the cell (Refractive index feature). The attenuation is a feature describing the optical intensity loss caused by cell absorption (Absorption-1 feature). Comparison of 3D and 2D scatter plots reveal that additional biophysical features serve to classify the cell types more accurately. It is clear that additional dimensions improve the level of distinguishing (distinguishment) among different cell types compared to individual features.

It should be noted that this figure, as well as others herein, depict these dots in shading due to the restrictions of the patent application process, although the original figures depict the plots in color, such as in the above figure with dots of red and black with (2D) projections onto each pair of biophysical feature planes in green and blue.

The cell diameter along the rainbow (Diameter-RB) is used as a size indicator. The cell protein concentration corresponds to the mean refractive index difference of the cell. The attenuation is a feature describing the optical intensity loss caused by cell absorption. Comparison of 3D and 2D scatter plots reveal that additional biophysical features serve to classify the cell types more accurately.

Figure 7A:
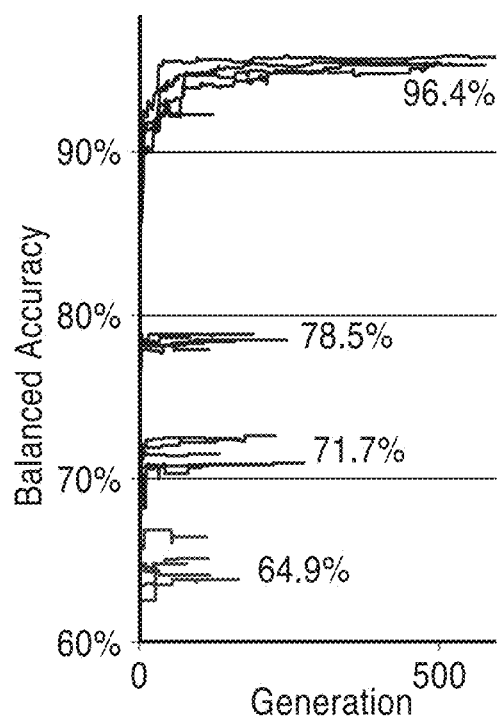
FIG. 7A through FIG. 7C are plots of accuracy, sensitivity, and component analysis in label-free classification found according to an embodiment of present disclosure.
Figure 7B:
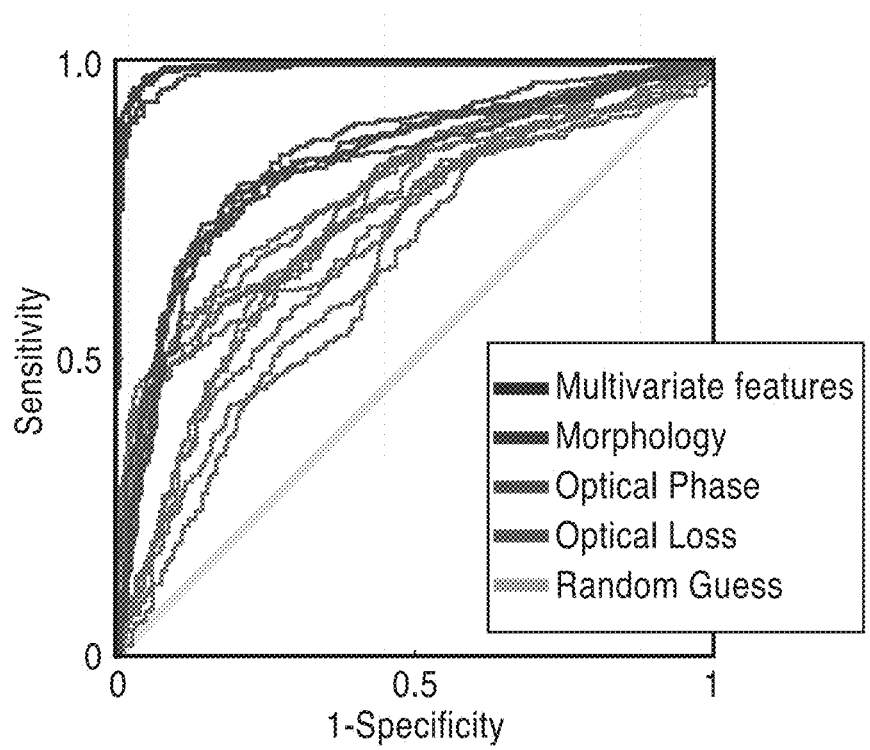
Figure 7C:
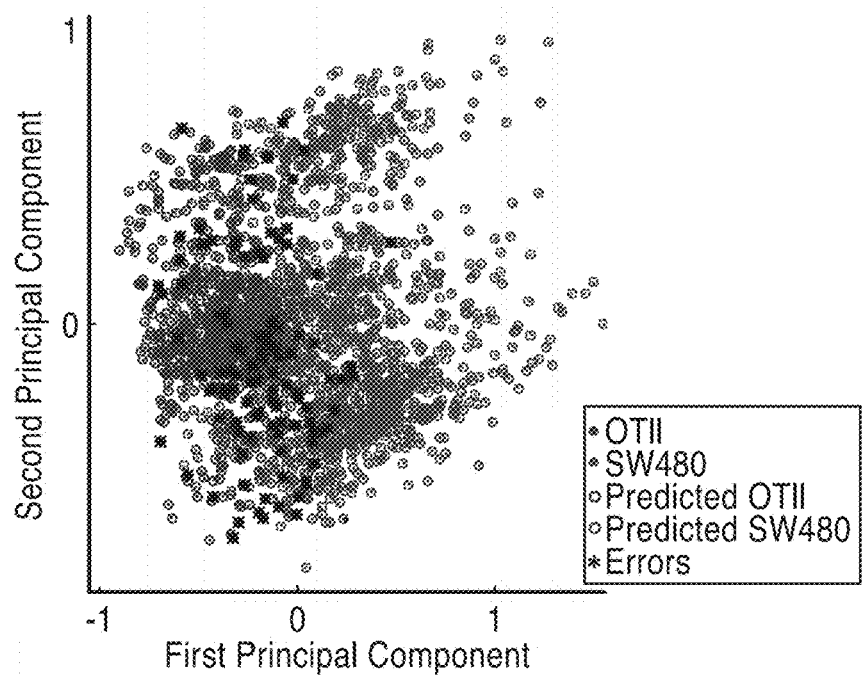

FIG. 7A through FIG. 7C show progress in label-free classification depicted by balanced accuracy in FIG. 7A, sensitivity and specificity in FIG. 7B, and principle component analysis in FIG. 7C. A five-fold cross-validation methodology is applied on the dataset to split data points into training, validation, and test subsets.

Referring to FIG. 7A, the progress of in label-free classification is depicted by balanced accuracy as the learning model evolves over genetic algorithm (GA) generations. A training process of the neural network leads to improvements in classification accuracy over generations of the genetic algorithm. In addition, in this present example the multivariate analysis uses all 16 biophysical features extracted from the TS-QPI quantitative images (uppermost set of curves). It will be appreciated that additional, or fewer, biophysical features, along with different selections and/or definitions of these biophysical features, can be similarly utilized without departing from the teachings of the present disclosure. Also shown is a training process by using three single features, seen in the lower curve sets, morphology (Diameter-RB), optical phase (OPD-1), and optical loss (Absorption-2). The values represent average balanced accuracy among training datasets at the end of optimization. Clearly, the final achievable accuracy by multivariate classification is considerably higher than that of single features.

To highlight the improvement by hyperdimensional feature space of TS-QPI, the balanced accuracy curves are shown in the figure based on several single features: cell diameter for morphology is depicted in the second set of curves seen near the 80% scale marking, integral of a cell's optical path difference for optical phase information in the third set down adjacent the 70% scale marking, and cellular absorption for optical loss in near-infrared window seen with the curves at the bottom of that figure. Although these three biophysical features individually perform the highest accuracy among morphology, optical phase, and optical loss groups respectively, as previously shown, the disclosed multivariate deep learning classifier outperforms them.

In FIG. 7B receiver operating characteristic (ROC) curves for each fold are generated based on the test subsets, and reveal the superior sensitivity and specificity of multivariate classifier. Also, the small variations of the ROC curves among different folds show the consistency of the classification performance for different test datasets. The upper set of curves here indicates Multivariate Features, with the next highest peaking set being Morphology, followed by Optical Phase, and then Optical loss. For comparison purposes a diagonal is also seen in the figure which statistically represents results from a random guess classification.

FIG. 7C illustrates a visualization of the hyperspace decision boundary, OT-II and SW-480 data points are shown in first and second principal components analysis (PCA) components.

2.5 Demonstration in Algal Lipid Content Classification

Microalgae are considered one of the most promising feedstock for biofuels. The productivity of these photosynthetic microorganisms in converting carbon dioxide into useful carbon-rich lipids greatly exceeds that of agricultural crops. Worldwide, research and demonstration programs are being carried out to develop the technology needed to expand algal lipid production as a major industrial process. Selecting high-yield microalgae with fast growth factors are essential in the biofuel production industry. Because algae differ greatly in size and structure, cell size alone provides insufficient information for cell classification.

Adding optical phase and loss data, obtained by the phase contrast time stretch imaging flow cytometer, to size data enables algal cells to be distinguished on the basis of lipid content. To test the disclosed apparatus for its ability to separate algal cells with high and low-lipid content, the starch-null sta6 strain of *Chlamydomonas reinhardtii* was exploited. This strain is deleted for sta6 (encoding the small subunit of ADP-glucose-pyrophosphorylase), and when nitrogen-deprived accumulates more lipid than wild-type. Comparison of the two strains therefore provides an ideal setup to test the ability to distinguish lipid-content phenotypes according to the disclosure.

Figure 8A:
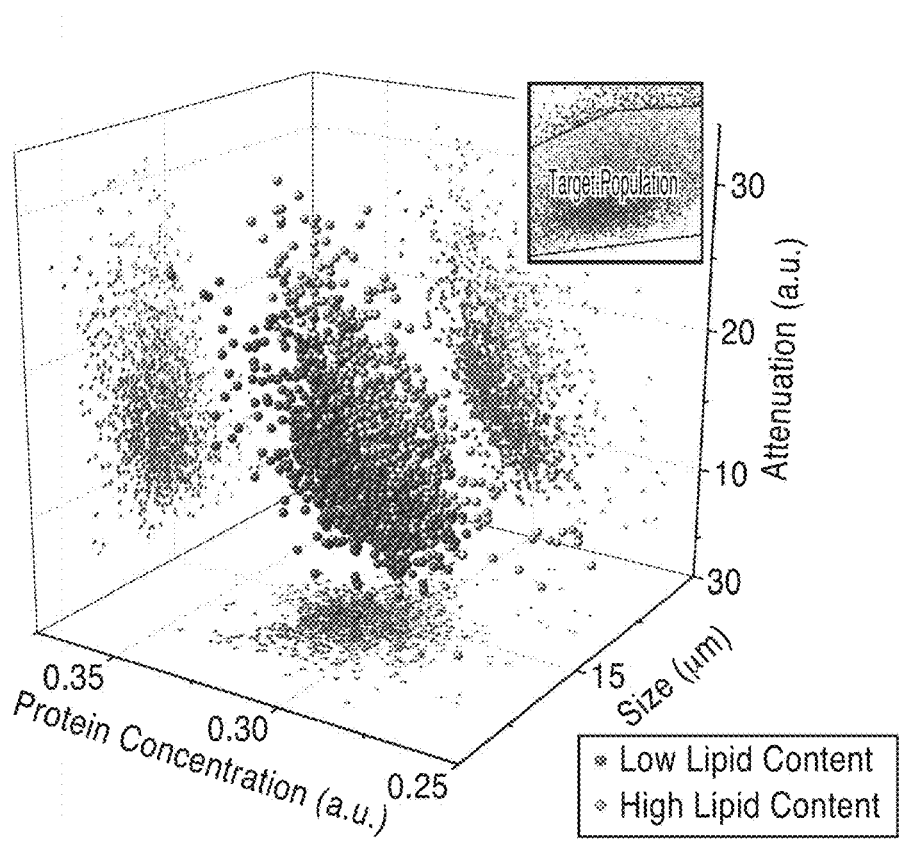
FIG. 8A and FIG. 8B are plots comparing features obtained for an example algal population obtained according to an embodiment of present disclosure.

FIG. 8A depicts a 3D scatter plot showing the three principal biophysical features for the two algal populations based on their lipid content as determined by TS-QPI. Here, the optical loss category of the features play a dominant role in label-free classification. This three-dimensional scatter plot based on size, protein concentration, and attenuation of the cells measured by TS-QPI, is shown with 2D projections for every combination of two features. The inset shows that conventional label-free flow cytometry using forward scattering and side scattering is not enough to distinguish the difference between high-lipid content and low-lipid content algal cells. The disclosed TS-QPI method is significantly more effective in separating the two algae populations.

Figure 8B:
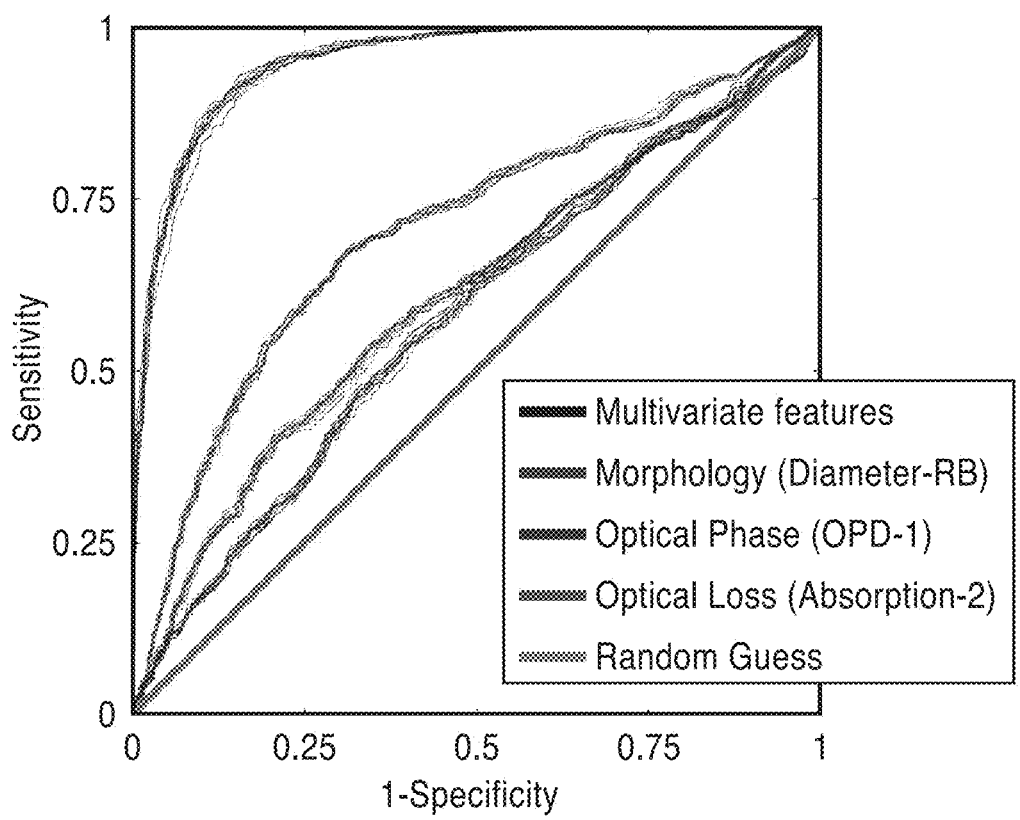

FIG. 8B depicts ROC curves for binary classification of these populations using ten-fold cross validation. The top most curves (closest to upper left corner) show the classifier performance using all 16 biophysical features extracted from the TS-QPI images. The subsequently lower plots in this figure show classifier decisions made using only the three major biophysical features: diameter for morphology (Diameter-RB), optical path length difference for optical phase (OPD-1), and absorption for optical loss (Absorption-2). It is seen that the disclosed multivariate deep learning using TS-QPI is far more accurate than individual biophysical characteristics for selection of algal strains. It should be appreciated that the label-free selection of algal strains improves as more biophysical features are employed.

2.6 Discussion

To show the effect of the training dataset size in the performance of the learning model, the learning curves for the training and test datasets of the tumor cell detection are analyzed.

Figure 9A:
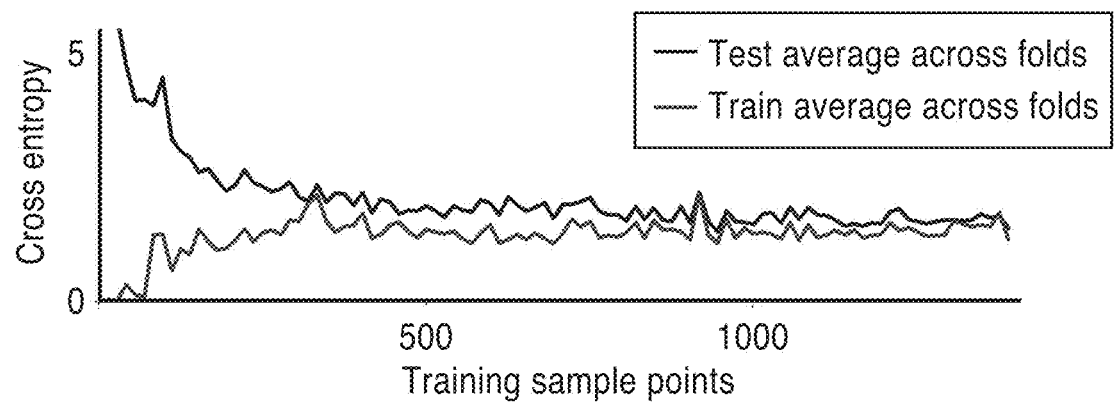
FIG. 9A and FIG. 9B are plots of testing and training averages with respect to number of points (FIG. 9A) and a comparison of balanced accuracy for an embodiment of the present disclosure compared with other techniques (FIG. 9B).

FIG. 9A depicts a test learning curve, obtained during tumor cell detection, with a test average across folds curve on top under which the train average across folds curve is seen, with cross entropy plotted with response to the number of sample training points. It can be seen from this figure that as the number of training data points increases, the test error reduces and the model performance improves. On the other hand, the training error contrastingly increases for a larger number of training examples because it is more difficult for the learning model to fit many training data points than a few. Larger number of training data points decreases the cross entropy of the test dataset, which means the classifier is performing more accurately; however, the trend is opposite for the training dataset because the fitting error accumulates with a larger number of training data points. The discrepancy of the training and test errors is the generalization error of the learning model. Notice that beyond $N \approx 850$ the generalization error does not decrease, and the learning curves converge to their ultimate performances. In other words, $N \approx 850$ training data points are required to accomplish target achievable performance for the deep learning model used here in this example.

Figure 9B:
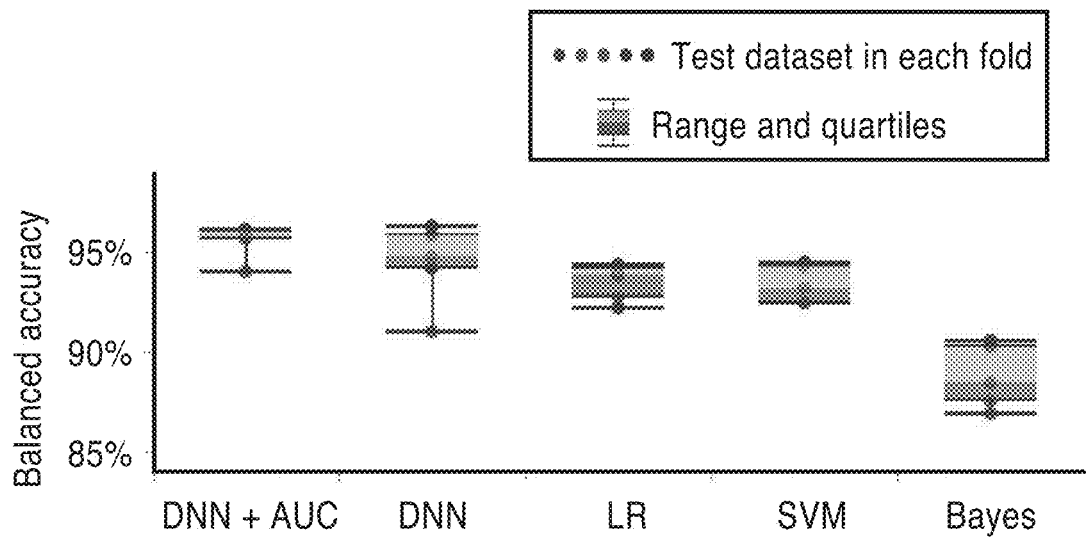

FIG. 9B illustrates a comparison between multiple machine learning classification techniques based on the biophysical features extracted from the label-free cell images captured by TS-QPI. The disclosed AUC-based deep learning model (DNN+AUC) has both the highest accuracy and consistency compared with support vector machine (SVM) with Gaussian kernel, logistic regression (LR), naive Bayes (Bayes), and conventional deep neural network trained by cross entropy and backpropagation (DNN).

It will be noted from the figure that the mean accuracies of all learning models are beyond 85%, reflecting the advantages of simultaneous hyperdimensional biophysical features that TS-QPI provides for label-free cell classification. Furthermore, the interquartile range of the balanced accuracy (shown with box plot) is the smallest for the regularized AUC-based deep learning model, which confirms its consistency and repeatability are the best among learning methods.

2.7 Conclusions on TS-QPI

Time-stretch quantitative phase imaging (TS-QPI) is capable of capturing images of flowing cells with minimal motion distortion at unprecedented rates of 100,000 cells/s. TS-QPI relies on spectral multiplexing to simultaneously capture both phase and intensity quantitative images in a single measurement, generating a wealth of information of each individual cell and eliminating the need for labeling with biomarkers. In this disclosure the information content of these images has been summarized in a set of 16 features for each cell, and classification performed in the hyperdimensional space composed of these features. Applications of various learning algorithms were demonstrated, including deep neural networks, support vector machine, logistic regression, naive Bayes, as well as a new training method based on area under the ROC curve. The results from two experimental demonstrations, one on detection of cancerous cells among white blood cells, and another one on identification of lipid-rich algae, show that classification accuracy by using the TS-QPI hyperdimensional space is more than 17% better than the conventional size-based techniques. The disclosed system opens the way to cellular phenotypic analysis as well as data-driven diagnostics, and thus, is a valuable tool for high-throughput label-free cell screening in medical, biotechnological, and research applications.

2.8 Methods of TS-QPI

An example embodiment of the disclosed time stretch quantitative phase imaging (TS-QPI) system was discussed in a previous section in relation to FIG. 1 and FIG. 2A through FIG. 2C. The following provides additional details regarding a specific example of this method.

Broadband optical pulses from a mode-locked laser (center wavelength=1565 nm, repetition rate=36.6 MHz, pulse width approximately 100 fs) are broadened using a highly nonlinear fiber to approximately 100 nm bandwidth with a spectral range up to 1605 nm. These broadband pulses are then linearly chirped to nanosecond pulse width by a short dispersion compensating fiber (DCF) of 60 ps/nm, so that an erbium doped fiber amplifier (EDFA) can amplify them with minimal distortion. A coarse wavelength division multiplexer (WDM) filters the pulses from 1581 nm to 1601 nm, where the spectrum is reasonably flat. Therefore, the total bandwidth of the pulses interrogating the cells in the exemplified setup is less than 20 nm centered at 1591 nm, yielding a negligible fractional bandwidth of 1.3%. These filtered pulses then pass through an optical circulator and are coupled to free-space with a fiber collimator.

Free-space laser pulses were linearly polarized with quarter- and half-wave plates, and then spatially dispersed with a pair of reflection diffraction gratings, so that each wavelength component of the collimated beam was positioned at a different lateral point similar to a line flash rainbow. A beam reducer shrank the rainbow beam six times with a pair of 90 degree off-axis parabolic gold-coated mirrors with reflected focal lengths of 152.4 mm and 25.4 mm, respectively. Next, a 15 degree off-axis parabolic gold-coated mirror with 635 mm reflected focal length and a long working-distance objective lens with 0.4 numerical aperture further shrank the rainbow to about 130 in width, i.e., field of view (FOV). Reflective optics with parabolic gold-coated mirrors are utilized in these experimental demonstrations to minimize loss, aberration, and polarization sensitivity.

Rainbow flashes were split into the two arms of a Michelson interferometer by a beam splitter. In the sample arm, the rainbow pulses pass through the cells and are reflected by the reflective substrate of the microfluidic device. In the reference arm, a dielectric mirror reflected the rainbow with a length mismatch with the sample arm causing spectral interference fringes, (seen in FIG. 10A). Cells are hydrodynamically focused at the center of the channel flow at a velocity of 1.3 m/s. The reflected pulses from reference and sample arms were recombined at the beam splitter, compressed by the two diffraction gratings and coupled back into the fiber. These return pulses were spectrally encoded by the spatial information of the interrogation field of view. Then they were redirected by the optical circulator to a Raman-amplified time-stretch dispersive Fourier Transform (TS-DFT) system followed by a 10 Gb/s photodetector (Discovery Semiconductors® DSC-402APD). An analog-to-digital converter (Tektronix® DPO72004C) with a sampling rate of 50 GS/s and 20 GHz bandwidth is used to acquire the output signal of the photodetector, which is a series of spectral interferograms mapped into time (seen in FIG. 10B).

2.8.1 Coherent Detection and Phase Extraction

Unlike conventional heterodyne detection, which uses a narrowband continuous-wave signal as the local oscillator or reference, the coherent detection in the disclosed time stretch system uses an unmodulated copy of the original optical input, which is a broadband optical pulse train.

Since the spectrum is mapped into space by diffraction gratings, the complex field at any specific spatial location within the field of view is a narrowband optical wave. As the envelope of the optical wave varies slowly in time compared to the period of the optical electromagnetic wave and the time mismatch between the reference arm and the sample arm, a slowly varying envelope approximation is employed in the present analysis. The complex envelope of the input electric field, $\tilde{E}_{in}(\omega, t_p)$, is split into two arms of the Michelson interferometer at the beam splitter. Here, $\omega$ is the optical frequency of the input signal, which corresponds to the spatial location x being interrogated by the optical wave at this frequency (i.e., spectral encoding of the object image). $t_p$ specifies the time when each rainbow flash reaches the beam splitter, corresponding to the p-th incoming pulse. Note that $\tilde{E}_{in}(\omega, t_p)$ can be simplified as $\tilde{E}_{in}(\omega)$ when pulse shape is stable from pulse to pulse. The light split into the two arms of the Michelson interferometer can be expressed as:

Into the sample arm:

$$\tilde{E}_s(\omega,t_p) = \sqrt{T_b}\tilde{E}_{in}(\omega,t_p) \tag{3}$$

Into the reference arm:

$$\tilde{E}_r(\omega,t_p) = i\sqrt{1-T_b}\tilde{E}_{in}(\omega,t_p)$$

where $T_b$ is the power transmission ratio of the beam-splitter. Optical intensity in the sample arm will be altered by the absorption and scattering of imaged cells, as well as that of the microfluidic channel and buffer solution. After passing through semi-transparent objects, not only will the electric field amplitude be modulated by the optical attenuation in the sample arm, but also the optical path length difference will lead to a phase shift, $\Delta\varphi_c(x, t_p)$, induced by refractive index change caused by the object along the interrogation beam. Thus, the complex fields of the light waves coming back to the beam splitter become:

From the sample arm:

$$\tilde{E}_s(\omega, t_p) = T_s(\omega)T_c(x, t_p + t_d)\sqrt{T_b(\omega)R_m(\omega)}$$

$$\tilde{E}_{in}(\omega, t_p) \cdot \exp\left\{i\left[-\frac{\omega}{c} \cdot 2(L + \Delta L) - \Delta\varphi_c(x, t_p)\right]\right\}$$

From the reference arm:

$$\tilde{E}_r(\omega, t_p) = i\sqrt{1 - T_b(\omega)}\sqrt{R_m(\omega)}\tilde{E}_{in}(\omega, t_p) \cdot \exp\left(-i\frac{\omega}{c} \cdot 2L\right) \tag{4}$$

where L is the length of reference arm, and $\Delta L$ is the arm length mismatch between two arms. $R_m(\omega)$ is the wavelength-dependent reflectance of the reflective substrate of the microfluidic channel and the dielectric mirror in the reference arm. $t_d$ is the time delay during which rainbow flash travels from the beam splitter to the sample cell, $$t_d = \frac{L_0 + \Delta L}{c} \cdot T_s(\omega)$$

is power transmittance of the surrounding buffer solution and microfluidic channel, and $T_c(x, t_p+t_d)$ is spatial power transmittance of cells at location x along the rainbow when being illuminated at time $t_p+t_d$. Both $\sqrt{T_s(\omega)}$ and $\sqrt{T_c(x,t_p+t_d)}$ affect the optical field twice as each rainbow flash passes through the cell twice. Since the $t_d$ is much smaller than the time scale of the envelope variations caused by the cell flow, we can approximate $T_c(x, t_p+t_d)$ to be $T_c(x, t_p)$, without sacrificing accuracy.

After the pulses from the two arms of the interferometer recombine at the beam splitter, the total electric field at each wavelength or optical frequency becomes:

$$\tilde{E}_0(\omega, t_p) = T_s(\omega)T_c(x, t_p)T_b(\omega)\sqrt{R_m(\omega)}\,\tilde{E}_{in}(\omega, t_p) \cdot \quad (5)$$
$$\exp\{i[-\frac{\omega}{c}\cdot 2(L+\Delta L) - \Delta\varphi_c(x, t_p)]\} -$$
$$[1-T_b(\omega)]\sqrt{R_m(\omega)}\,\tilde{E}_{in}(\omega, t_p)\exp[-i\frac{\omega}{c}\cdot 2L]$$
$$= \sqrt{R_m(\omega)}\,\tilde{E}_{in}(\omega, t_p)\exp\left(-i\frac{2\omega L}{c}\right)\cdot$$
$$\{T_s(\omega)T_c(x, t_p)T_b(\omega)\exp\{i[-2\frac{\omega}{c}\Delta L -$$
$$\Delta\varphi_c(x, t_p)]\} - [1-T_b(\omega)]\}.$$

Based on the spectral encoding setup, it is known that spatial information has been encoded into spectrum, $$T_c(x,t_p) \Rightarrow T_c(\omega,t_p) \quad (6)$$

$$\Delta\varphi_c(x,t_p) \Rightarrow \Delta\varphi_c(\omega,t_p) \quad (7)$$

the intensity envelope then becomes $$\tilde{I}_o(\omega,t_p) \propto \tilde{E}_o(\omega,t_p) = \{[1-T_b(\omega)]^2 + T_b^2(\omega)T_c^2(\omega,t_p)T_s^2(\omega)\}R_m(\omega)\cdot|\tilde{E}_{in}(\omega,t_p)|^2 - 2[1-T_b(\omega)]T_c(\omega,t_p)T_b(\omega)\,R_m(\omega)\cdot T_s(\omega)|\tilde{E}_{in}(\omega,t_p)|^2 \cos[2\omega\Delta L/c + \Delta\varphi_c(\omega,t_p)] \quad (8)$$

During time stretching, each frequency component ω, or wavelength λ will be one-to-one mapped into the time domain. The relative time delay of λ is defined compared to the central wavelength, $\lambda_c$, as $l_i$, which is usually called intra-pulse time delay. Written in terms of λ, Eq. 8 can be simplified as $$\tilde{I}_o(\lambda, t_p) \propto I_b(\lambda, t_p) + I_i(\lambda, t_p)\cos\left[\frac{4\pi\Delta L}{\lambda} + \Delta\varphi_c(\lambda, t_p)\right] \quad (9)$$

where $I_b(\lambda, t_p)$ is the background or baseband intensity envelope, and $I_i(\lambda, t_p)$ is the interference or intermediate intensity envelope:

$$I_b(\lambda, t_p) = \{[1-T_b(\lambda)]^2 + T_b^2(\lambda)T_c^2(\lambda, t_p)T_s^2(\lambda)\}\cdot R_m(\lambda)[\tilde{E}_{in}(\lambda, t_p)]^2 \quad (10)$$

$$I_i(\lambda, t_p) = -2[1-T_b(\lambda)]T_c(\lambda, t_p)T_b(\lambda)R_m(\lambda)\cdot T_s(\lambda)[\tilde{E}_{in}(\lambda, t_p)]^2 \quad (11)$$

The linear time stretch maps frequency domain into time domain by $$t_i = D(\lambda - \lambda_c)L_f \quad (12)$$

Here $\lambda_c$ is the central wavelength and $L_f$ is the length of the dispersive fiber. D is the group velocity dispersion, that is, the temporal pulse spreading, $\Delta t_i$, per unit bandwidth, per unit distance traveled. Thus the temporal samples of the energy flux absorbed at the photodetector are the intra-pulse concatenation of spectral samples followed by inter-pulse concatenation of pulse waveforms:

$$\tilde{I}_{PD} = \text{cat\_cat}_\downarrow \begin{pmatrix} \tilde{I}_o(t_i^{(1)}, t_p^{(1)}) & \tilde{I}_o(t_i^{(1)}, t_p^{(2)}) & \cdots & \tilde{I}_o(t_i^{(1)}, t_p^{(m)}) \\ \tilde{I}_o(t_i^{(2)}, t_p^{(1)}) & \tilde{I}_o(t_i^{(2)}, t_p^{(2)}) & \cdots & \tilde{I}_o(t_i^{(2)}, t_p^{(m)}) \\ \vdots & \vdots & \ddots & \vdots \\ \tilde{I}_o(t_i^{(n)}, t_p^{(1)}) & \tilde{I}_o(t_i^{(n)}, t_p^{(2)}) & \cdots & \tilde{I}_o(t_i^{(n)}, t_p^{(m)}) \end{pmatrix} \quad (13)$$

$$\rightleftharpoons \text{cat\_cat}_\downarrow \begin{pmatrix} \tilde{I}_o(\lambda_1, t_p^{(1)}) & \tilde{I}_o(\lambda_1, t_p^{(2)}) & \cdots & \tilde{I}_o(\lambda_1, t_p^{(m)}) \\ \tilde{I}_o(\lambda_2, t_p^{(1)}) & \tilde{I}_o(\lambda_2, t_p^{(2)}) & \cdots & \tilde{I}_o(\lambda_2, t_p^{(m)}) \\ \vdots & \vdots & \ddots & \vdots \\ \tilde{I}_o(\lambda_n, t_p^{(1)}) & \tilde{I}_o(\lambda_n, t_p^{(2)}) & \cdots & \tilde{I}_o(\lambda_n, t_p^{(m)}) \end{pmatrix}$$

where cat and cat↓ mean horizontal and vertical concatenations, respectively. Each $\tilde{I}_o(t_i^{(n)}, t_p^{(m)})$ expresses the nth spectral (spatial) pixel at the mth pulse (line image). Applying Eq. 12 to Eq. 9, $$\tilde{I}_o(t_i^{(n)}, t_p^{(m)}) \propto I_b(t_i^{(n)}, t_p^{(m)}) + \quad (14)$$
$$I_i(t_i^{(n)}, t_p^{(m)}) \cdot \cos\left[\frac{4\pi\Delta L \cdot DL_f}{t_i^{(n)} + D\lambda_c L_f} + \Delta\varphi_c(t_i^{(n)}, t_p^{(m)})\right]$$

Therefore, the time stretched temporal waveform corresponding to each line scan image consists of two features. One is a $I_b(t_i^{(n)}, t_p^{(m)})$, a temporal envelope of the time-stretched optical pulse at baseband frequencies. The amplitude of this envelope corresponds to the temporal shape of the optical pulse and its deviations caused by the object transmission as in brightfield microscopy. It provides information about optical loss, for instance light absorption and scattering caused by surface roughness, granularity, and inner cell organelle complexity.

The second term in Eq. 14 (with cosine component) is a fast oscillating fringe, caused by the spectral interference of the recombined pulses from the sample and the reference arms in the Michelson interferometer. This term can be separated by a bandpass filter, and its envelope can be derived by a nonlinear envelope detection technique. By way of example and not limitation, a moving minimum/maximum filter was utilized to extract the envelope. After normalization to the envelope, the cosine component $$I_c(t_i^{(n)}, t_p^{(m)}) = \cos\left[\frac{4\pi\Delta L \cdot DL_f}{t_i^{(n)} + D\lambda_c L_f} + \Delta\varphi_c(t_i^{(n)}, t_p^{(m)})\right] \quad (15)$$

is used for calculation of the object phase shift, $\Delta\varphi_c(x,t_p)$. The first term in cosine causes the interferogram fringe pattern. Since $t_i \ll D\lambda_c L_f$, it can be approximated as $$\frac{4\pi DL_f \Delta L}{I_i + D\lambda_c L_f} \cong f_i t_i + \varphi_{i0} \quad (16)$$

where $\varphi_{i0}$ is an initial phase constant, $f_i$ is the fringe frequency:

$$f_i \cong \frac{4\pi \Delta L}{\lambda_c^2 DL_f} \quad (17)$$

Figure 10A:
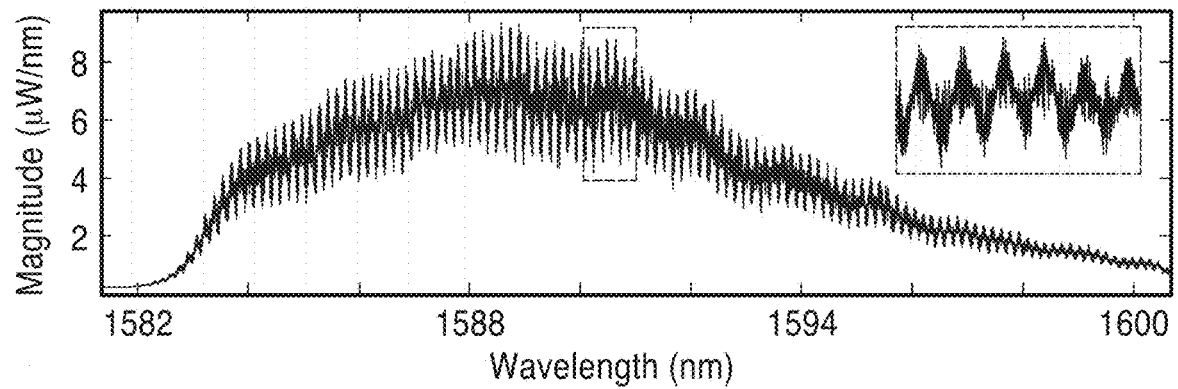
FIG. 10A and FIG. 10B are plots of spectral interference fringes and associated spectral interferograms as determined according to an embodiment of the present disclosure.
Figure 10B:
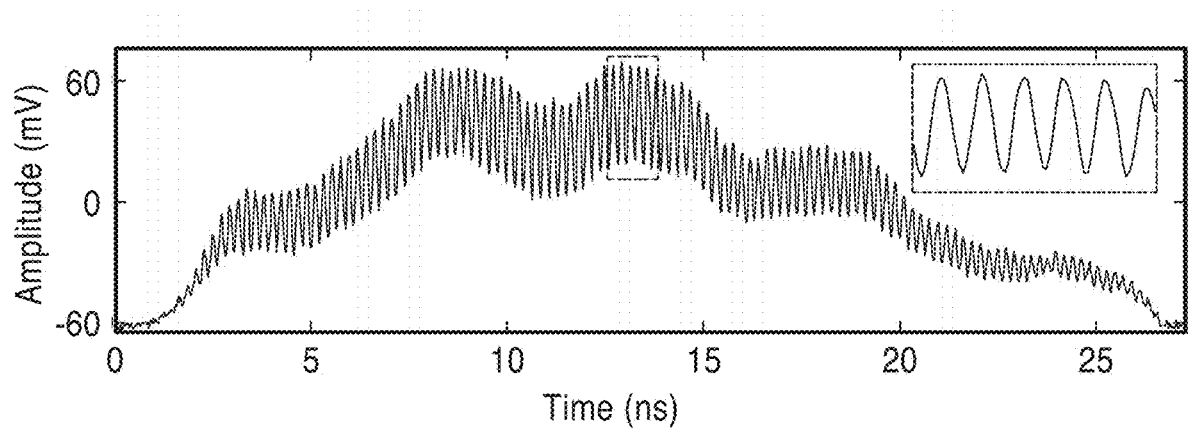

As seen in FIG. 10B, the fringe frequency, $f_i$, in our setup is about 4.7 GHz determined by the optical path length mismatch between the interferometer arms.

The instantaneous phase of $I_c(t_i^{(n)}, t_p^{(m)})$ can be readily retrieved from its analytic representation given by Hilbert transform, $\mathcal{H}$:

$$\angle I_c(t_i^{(n)}, t_p^{(m)}) = \arg[I_c(t_i^{(n)}, t_p^{(m)}) + j \cdot \mathcal{H}\{I_c(t_i^{(n)}, t_p^{(m)})\}] \quad (18)$$
$$= \frac{4\pi D L_f \Delta L}{t_i^{(n)} + D\lambda_c L_f} + \Delta\varphi_c(t_i^{(n)}, t_p^{(m)})$$

here arg means the argument of a complex number. A one-dimensional phase unwrapping algorithm followed by background phase removal gives the object phase shift, $$\Delta\varphi_c(t_i^{(n)}, t_p^{(m)}) = \text{unwrap}\{\angle I_c(t_i^{(n)}, t_p^{(m)})\} - \text{unwrap}\{\angle I_c(t_i^{(n)}, t_p^{(empty)})\} \quad (19)$$

where $t_p^{(empty)}$ corresponds to an empty pulse when no cell is in the field of view, for example background phase. The unwrapping algorithm used in the disclosed processing acts when the absolute phase difference between two consecutive samples of the signal is greater than or equal to π radians, and adds multiples of 2π to the following samples in order to bring the consecutive sample phase differences in the acceptable range of -π to π.

To perform combined quantitative phase and loss imaging, the phase derived by Hilbert transformation should be corrected to eliminate the artifacts caused by the intensity variations induced by the passing cells. Most cells of interest in clinical or industrial applications have a diameter of about 3 μm to 40 μm, when suspended in fluid. Given the field of view and the period of the interrogation rainbow pulses are 130 μm and 27 ns, respectively, the time duration of the instantaneous intensity change induced by the single cells in each laser pulse is approximately 0.6 ns to 8.3 ns, which will generate baseband frequency components up to about 1.6 GHz. Compared to the higher frequency components at 4.7 GHz corresponding to the interference fringes, the frequency of intensity variations is small (less than about 1.6 GHz), and in this scenario, the disclosed method remains robust to separate the two electrical spectral components for optical loss and phase.

2.8.2 Cell Transmittance Extraction

One of the advantages of TS-QPI is its ability to extract the cell transmittance, $T_c(\lambda)$ without prior knowledge of the transmittance of the solution, $T_s(\lambda)$, that of the beamsplitter, $T_b(\lambda)$, and the reflectance of substrate of the microfluidic channel, $R_m(\lambda)$. During measurements when there is no cell in the field of view (empty frames), Eq. 11 becomes $$I_i(\lambda, t_p^{(empty)}) = -2[1 - T_b(\lambda)]T_b(\lambda)R_m(\lambda) \cdot T_s(\lambda) |\tilde{E}_{in}(\lambda, t_p^{(empty)})|^2 \quad (20)$$

In addition, the signal from only the reference arm can be recorded by blocking the sample arm:

$$I_r(\lambda, t_p) = [1 - T_b(\lambda)]^2 R_m(\lambda) |\tilde{E}^{in}(\lambda, t_p)|^2 \quad (21)$$

Combining Eqs. 10, 20, and 21, and assuming that the input electric field pulse shape, $|\tilde{E}_{in}(\lambda, t_p)|$, is invariant to $t_p$, the cell transmittance can be derived as $$T_c(x) = T_c(\lambda) = \frac{-\sqrt[2]{I_r(\lambda, t_p) \cdot (I_b(\lambda, t_p) - I_r(\lambda, t_p))}}{I_i(\lambda, t_p^{(empty)})} \quad (22)$$

Please note that the values of $I_r(\lambda, t_p)$, $I_b(\lambda, t_p)$, and $I_i(\lambda, t_p^{(empty)})$ are directly measured by TS-QPI, and no prior knowledge of $T_b(\lambda)$, $T_s(\lambda)$, $R_m(\lambda)$, and $|\tilde{E}_{in}(\lambda, t_p)|$ is required for determining cell transmittance.

2.8.3 Image Reconstruction

The disclosed method provides for reconstructing both quantitative brightfield and phase-contrast images simultaneously from single-shot frequency-multiplexed interferometric measurements. The envelope and phase of the time-domain signal $\tilde{I}_o(t_i^{(n)}, t_p^{(m)})$ was first mapped into a series of spatial information $\tilde{I}_o(x^{(n)}, t_p^{(m)})$, forming linescan brightfield and phase-contrast images, illuminated by the optical pulse at time $t_p$. This is because within each optical pulse, the spatial information is mapped one-to-one into the spectral domain, $x^{(n)} \to \lambda_n$, and spectrum is stretched in time, $\lambda_n \to t_i^{(n)}$, where $t_i^{(n)}$ is the relative group delay time of each frequency component within a pulse with respect to the central wavelength. These line-scan images based on $\tilde{I}_o(x, t_p^{(1)})$, $\tilde{I}_o(x, t_p^{(2)})$, $\tilde{I}_o(x, t_p^{(3)})$, ... were then cascaded into a two dimensional image corresponding to $\tilde{I}_o(x, y)$ where the second dimension y is the spatial mapping of time lapse based on object flow speed.

The optical path length difference image can be calculated by the phase shift line scans as $$OPD(x^{(n)}, y^{(m)}) = \frac{\lambda(t_i^{(n)}, t_p^{(m)})}{2\pi} \Delta\varphi_c(t_i^{(n)}, t_p^{(m)}) \quad (23)$$

On the other hand, if the axial thickness of the cell at reconstructed image pixel (x, y) is t(x, y), $$OPD(x,y) = 2[n_{cell}(x,y) - n_{solution}(x,y)] \cdot t(x,y) \quad (24)$$

in which $n_{cell}$ and $n_{solution}$ are the refractive indices of the cell and the surrounding buffer solution, respectively. The factor two (2) is to account for the fact that each wavelength component passes the cell twice in Michelson interferometer.

If Eq. 24 is integrated over the area of the cell, then an average refractive index contrast for the cell can be derived, which corresponds to the average protein concentration of the cell:

$$\overline{\Delta n_{cell}} = \overline{n_{cell}} - n_{solution} = \frac{\iint_{cell} OPD(x, y) dx dy}{2 \iint_{cell} t(x, y) dx dy} \quad (25)$$

where $\iint_{cell} t(x, y) dx dy$ is the volume of the cell obtained from its lateral diameter, d, as $V \approx \pi d^3/6$.

The relative net change of intensity envelope variations induced by the cell is obtained from the amplitude of the baseband intensity envelope of the interferogram as $$\Delta I_b(\lambda, t_p) = \frac{T_b^2(\lambda) T_s^2(\lambda)(1 - T_c^2(\lambda, t_p))}{[1 - T_b(\lambda)]^2 + T_b^2(\lambda) T_s^2(\lambda)} \quad (26)$$

It gives the temporal and spatial information of the combined effects from absorption and scattering:

$$I_{loss}(x^{(n)}, y^{(m)}) = \Delta I_b(\lambda_n, t_p^{(m)}) \quad (27)$$

2.8.4 Big Data Analytics Pipeline

The high-content image analysis and cell screening pipeline is implemented by combining multiple informatics tools, namely Cell Profiler for image processing, MySQL/MangoDB for database, Matlab for machine learning, and Javascript for interactive visualization. First of all, image noise reduction and smoothing have been performed, which can remove artifacts that are smaller than the optical resolution limit. By way of example and not limitation, Otsu's thresholding method is utilized for object segmentation. Once objects are identified in the image, morphology of each single cell can be described by area, diameter, uniformity, aspect ratio, perimeter, number of surrounding clumped cells, and so forth.

The capability to identify clumped cells from single large cells greatly reduces the misclassification rate in imaging flow cytometry compared to traditional flow cytometry. Intensity peaks of pixel brightness within each object are used to distinguish clumped objects. The object centers are defined as local intensity maxima in the smoothed image. Retaining outlines of the identified objects helps validate and visualize the algorithm. In the next step, the objects touching the borders of the image, such as the edges of the field of view and data acquisition time window, are discarded. However, the chance of cells showing up at the edges is very low due to hydrodynamic focusing. The disclosed technology is also capable of excluding dust, noise, and debris by neglecting the objects that are too small or have extreme aspect ratios.

To calibrate the imaging system and image processing pipelines for size measurement, 5 μm polystyrene beads (from Polysciences, Inc.®) with National Institute of Standards and Technology (NIST) traceable particle size standards were analyzed. Size measurement of the polystyrene beads had a distribution with 5.06 μm expected mean and 0.5 μm standard deviation. The broadened standard deviation was within the range of optical resolution limit and was caused mainly by performing object recognition on resolution limited images. Due to limited optical resolution of the setup, the edges of bead or cell are blurred, generating distribution of point spread functions in optical phase and loss images outside of the cell boundaries. In order to maximize the accuracy in morphological, phase, and loss measurements, after object segmentation we expanded the object boundaries by 2.5 μm (optical resolution of the setup measured by knife-edge method), which serve as loose boundaries, indicating the area within which the pixel intensities are measured and integrated in phase and loss images.

2.8.5 Data Cleaning

Data cleaning includes two steps. Firstly, Hotelling's T-squared distribution is calculated and the top 2% of the extreme data was set as outliers due to experimental or object recognition errors. Secondly, debris discrimination is performed; any data point with negative phase shift was considered as either air bubble, flow turbulence, or object recognition errors.

3.0 Deep Learning in Label-free Cell Classification 3.1 Principle Component Analysis (PCA)

As was shown in FIG. 4A and FIG. 4B, many of the 16 features are correlated and not all measured features in the data set produced by the time stretch quantitative phase imaging have the same amount of information. That result suggests that it may be possible to reduce the 16 dimensional data set to a smaller set of uncorrelated orthogonal dimensions without significantly compromising the classification accuracy. Toward that goal principle component analysis (PCA) has been utilized in an embodiment of this disclosure for dimensionality reduction and computation speed-up. The PCA algorithm finds an alternative lower dimensional space, such that variance of data projected onto this subspace is maximized along subspace dimensions.

FIG. 10A and FIG. 10B depict a comparison of plots of the interference pattern (FIG. 10A) and its spectral domain being mapped linearly into the time domain (FIG. 10B).

In FIG. 10A spectral interference fringes are shown as captured by the TS-QPI apparatus, and with its optical spectrum after quantitative phase imaging and before it enters the amplified time-stretch system.

In FIG. 10B is shown the output after the spectral interferogram is linearly mapped into time by the disclosed technique. It will be noted that the baseband intensity envelope is slightly modified by the wavelength-dependent gain profile of the Raman amplifier. The insets of FIG. 10A and FIG. 10B show zoomed-in spectrum and waveform, respectively. Clearly, the single-shot interferogram measured by Raman-amplified time-stretch dispersive Fourier Transform has a higher signal-to-noise ratio compared to that captured by optical spectrum analyzer.

Figure 11A:
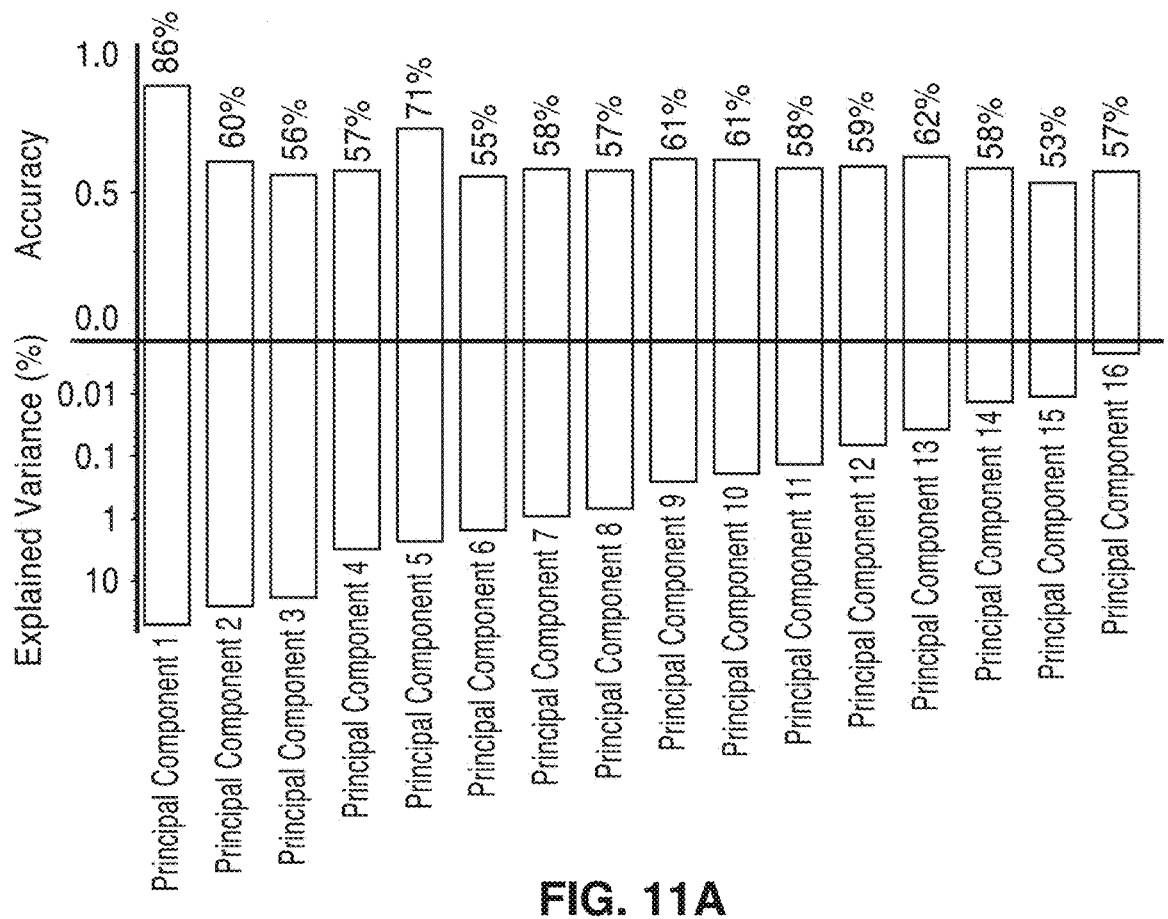
FIG. 11A and FIG. 11B are plots indicating variance for the principle classification parameters and accuracy increases with respect to number of classification parameters utilized according to an embodiment of the present disclosure.

FIG. 11A shows the percent of the variance in data explained by each component in the lower portion of the chart. The key observation is that most of the variance can be accounted for by the first two principle components. The upper portion of the plot shows the accuracy for binary classification using each of the principle components. Interestingly, the first component with the highest explained variance is not necessarily the most important component for classification. Therefore, a priori intuition about the physical significance of the features in the case here, is superior to PCA in eliminating dimensions that do not provide high value in classification. By revealing the structure in data that best explains the variance, PCA achieves data compression via dimensionality reduction.

Figure 11B:
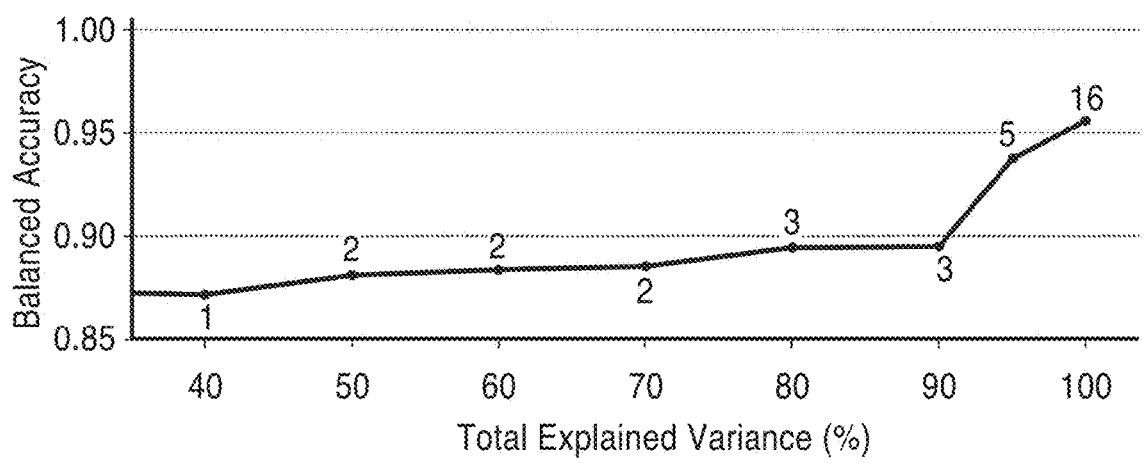

PCA components act as the input features for the classification method. As the number of PCA components retained increases, the classification accuracy improves while computation time increases (FIG. 11B). Since accuracy is the main objective in the primary examples of this disclosure, all 16 biophysical features are employed, rather than dimensionality-reduced PCA components. The value at each data point corresponds to the number of PCA components retained in order to achieve that total explained variance. In order to reduce the number of input features and decrease computation time, a subset of the PCA components can be used for classification. The classification accuracy improves as the total variance retained in the subset of PCA components increases. Nearly 90% accuracy can be achieved with the first three PCA components. The small deviation among accuracies of data points with the same number of PCA components are due to variations in random data partitioning.

3.2 Cross Validation

Figure 12A:
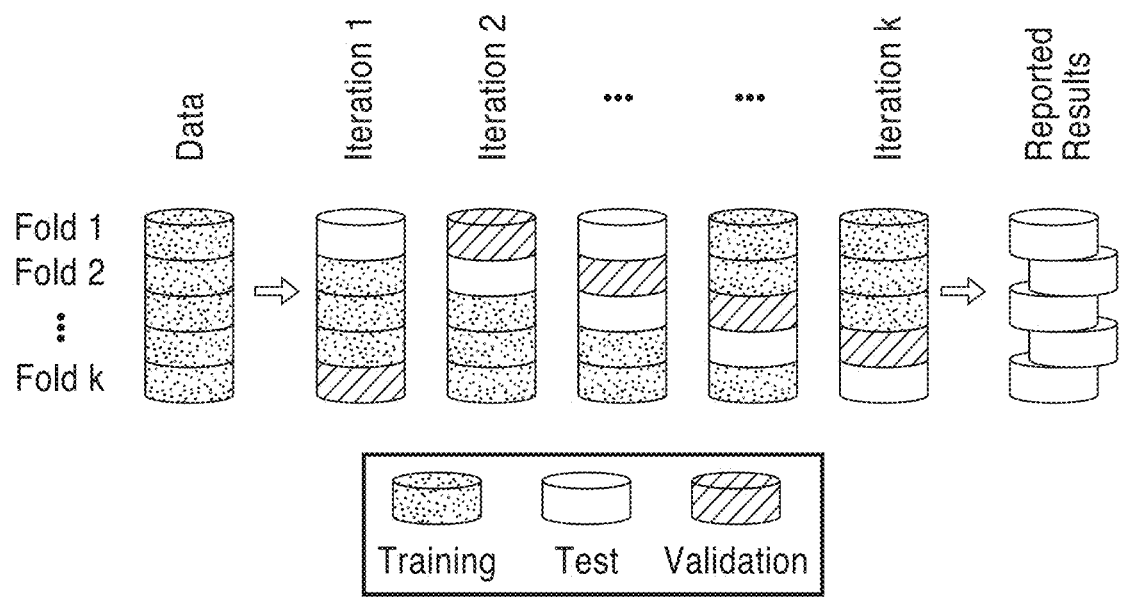
FIG. 12A and FIG. 12B are a diagram and plot of training and testing during tuning of a neural network utilized according to an embodiment of the present disclosure.
Figure 12B:
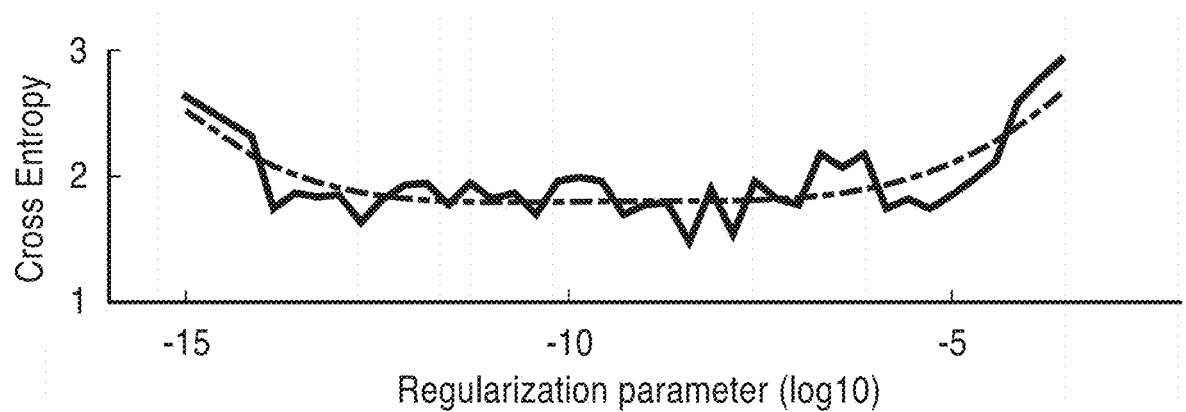

FIG. 12A and FIG. 12B illustrate training, test, and validation subsets across a number of iterations and folds (FIG. 12A), and network error changes in response to changes in regularization parameter (FIG. 12B).

The k-fold cross-validation implemented here splits data points into training, validation, and test subsets as seen in FIG. 12A. In each iteration, one fold is used for fine tuning the learning model (validation dataset), another fold is used for evaluation of the final results (test dataset), while the rest of the data points are used for training (training dataset). Thus, for each iteration, one fold is used as test data, one for validation while the other folds are used during training process. After being initially trained, the performance of the network is analyzed by the validation data to fine tune the neural network architecture and regularization parameter. The final reported results are aggregate of the outcomes from the test datasets.

In FIG. 12B it is seen that either a too small or a too large a regularization parameter λ increases network error due to overfitting or underfitting, respectively. A suitable regularization parameter λ balances the trade-off between overfitting (variance) and underfitting (bias) and minimizes the cross entropy of the validation dataset. Therefore, there is a suitable range of regularization parameter for each learning model.

Once the network architecture and regularization parameter are chosen and optimized based on the validation data, the learning model performance is finally verified by the test fold, which has never been utilized before in this iteration. The process of training in each iterations is independent, so each iteration has no prior knowledge about the chosen learning models in other iterations. The final reported results are aggregate of the performance for different test datasets.

3.3 Computation Time

The disclosed deep learning technique uses AUC as the cost function and performs training through a genetic algorithm. Since AUC is calculated based on the entire dataset, the genetic algorithm is employed as a global optimization method.

Thus, the disclosed technique has inherently higher accuracy and repeatability compared to conventional deep learning and other classification algorithms studied here. However, the global optimization is obtained with a higher computation time. The performance of balanced accuracy and computation time of different classification algorithms are compared in Table 1.

3.4 Performance and Resolvable Points

Lateral resolution of the time stretch camera is decided by the limiting factor among Abbe diffraction limit of the objective lens, spectral resolvability of the diffraction grating pairs, spectral resolution in amplified dispersive Fourier transform, the photodetector rise-time and bandwidth, and the sampling rate of the back-end digitizer.

Details of the limiting factors of lateral resolution and evaluation of these factors for our TS-QPI system can be found in Table 2. Field of view (FOV) is the area covered by the interrogation rainbow when the rainbow pulses hit the imaging plane. The rainbow pulse width is decided by the optical bandwidth selected from the laser source, $\Delta\lambda$, the magnification factor of the objective lens, the focal length of the other lenses and parabolic mirrors, as well as the dimensions and blaze angles of the diffraction gratings.

The resolution of phase measurement along the axial direction is determined by the effective number of bits (ENOB) of the digitizer and affected by the noise of laser source. Since pulse-to-pulse intensity and phase fluctuations are small, noise from laser source is not the limiting factor in our phase measurements. Supposing the ENOB of the digitizer is N, the minimum detectable optical path length difference, $\Delta L$ can be estimated as $$\frac{1}{2}\sin\left(\frac{4\pi\Delta L}{\lambda+\Delta\lambda/2}\right)=2^{-N} \qquad (28)$$

where λ is the central wavelength of light, and Δλ is the optical bandwidth. In the disclosed system, ENOB of the analog-to-digital converter is five by way of example and not limitation. Thus, the OPD resolution along the axial direction is about 8:0 nm, corresponding to refractive index difference down to the order of 0.001 for cellular level measurements.

3.5 Microfluidic Channel Design and Fabrication

The Polydimethylsiloxane (PDMS) microfluidic channel according to at least one example embodiment is custom-designed to fit into the reflective optics design. Cells are hydrodynamically focused at the center of the channel owing at a velocity of 1.3 m/s. The microfluidic device consists of a hydrodynamic focusing region and an imaging region targeted by the interrogation rainbow flashes in TS-QPI system. At the hydrodynamic focusing region, the sheath pressure focused the sample at the center of the channel by narrowing its row width from 200 μm to about 40 μm with a sheath to sample volume ratio of 3:1. The dimension of the channel was chosen as 200 μm (width)×25 μm (height) so that the cells will be imaged within depth of focus with a narrow lateral distribution. The size of the entire PDMS channel in the example embodiment is optimized for fitting on a 2 inch diameter dielectric mirror with sufficient space at the edges to achieve strong bonding. The thickness of the channel top layer is optimized for stabilizing peek tubes performance reliability while accommodating the working distance of the objective lens.

Figure 13A:
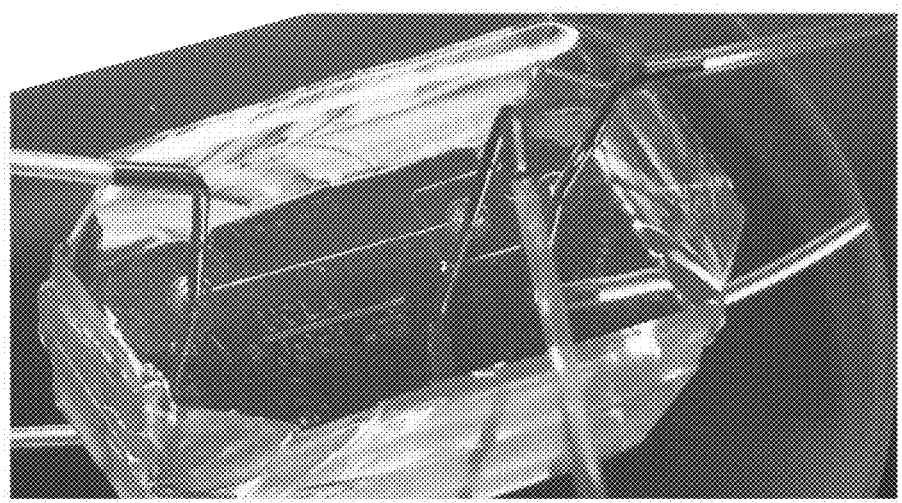
FIG. 13A and FIG. 13B are an image and 2D outline of a PDMS microfluidic channel according to an embodiment of the present disclosure.
Figure 13B:
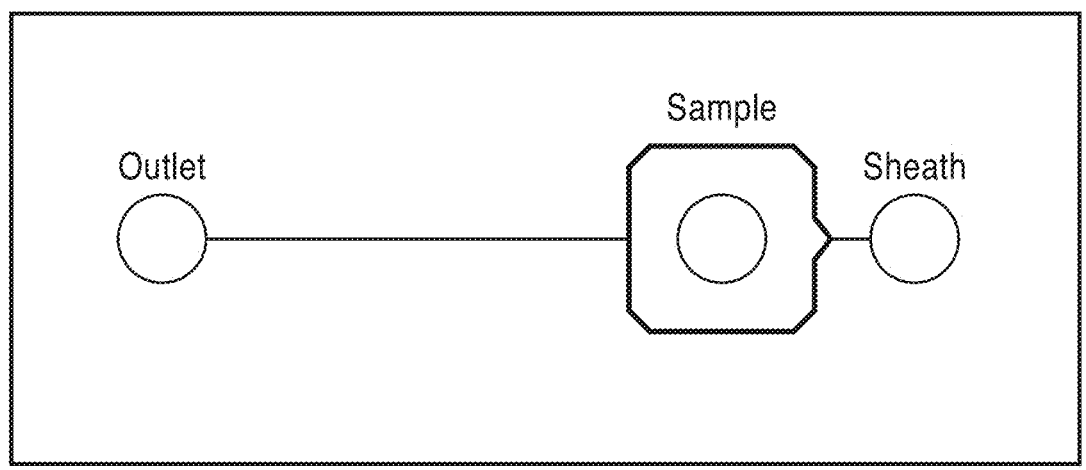

FIG. 13A and FIG. 13B illustrate an example embodiment of a PDMS microfluidic channel fabricated using standard soft lithography. In FIG. 13A is seen the PDMS microfluidic channel mounted on a highly reflective surface with near-infrared dielectric coating. The microfluidic device consists of a hydrodynamic focusing region and an imaging region targeted by the interrogation rainbow flashes in TS-QPI system. A sample solution is seen with suspended cells fed into the channel through the sample inlet, and deionized water as the sheath fluid injected through the sheath inlet. At the hydrodynamic focusing region, the sheath pressure focused the sample at the center of the channel by narrowing its flow width from 200 μm to about 40 μm with a sheath to sample volume ratio of 3:1.

In FIG. 13B the pattern of the mask is shown which was utilized to imprint microfluidic channel design on a silicon wafer with photoresist. The circles are inlet and outlet reservoirs. The mask was designed in AutoCAD® and printed with a resolution down to 1 μm. Then a 4-inch silicon wafer was spin-coated with 75 μm thickness of a negative photoresist (SU-8 from MicroChem®) and was exposed under the mask using an aligner. After post-exposure baking, the wafer was developed at room temperature, rinsed with isopropyl alcohol (IPA), and placed in a petri dish. A PDMS mixture (Sylgard 184™ Silicone Elastomer, Dow Corning®) was poured onto the patterned wafer, degassed in a vacuum chamber for 30 min and cured at 80° C. for one hour. Once cured, the PDMS channel was cut out and peeled off from the master wafer. In this example a 1:25 μm diameter hollow needle was utilized to punch the inlet and outlet holes. The punched PDMS channel was then cleaned with nitrogen gun and magic tape (3M), treated with oxygen plasma (Enercon® Dyne-A-Mite 3D Treater™) for 2 min, and bonded to a 2-inch diameter broadband dielectric mirror (Thorlabs® BB2-E04) for obtaining high reflectance from channel substrate at near infrared spectral window. Finally microtubes (PE-50 tubing, 0.023×0.038 in) with steel catheter couplers (Instech®, 22 ga×15 mm) are connected to the inlet and outlet punctures.

3.6 Preparation of Algae Cell Lines

*Chlamydomonas reinhardtii* strains used were cw15 (nit1 NIT2 mt$^{+-}$) and sta6 (cw15 nit1 NIT2 arg7-7 sta6-1::ARG7 mt+), available as CC-4568, CC-4348 respectively from the *Chlamydomonas* resource center (CRC).

Cells were grown in tris-acetate-phosphate (TAP) medium supplemented with arginine (100 µg/mL). Cultures were grown in Innova incubators (New Brunswick Scientific, Edison, N.J.) at 24° C., agitated at 180 rpm with continuous light (95 µmol/m²s, using six cool white fluorescent bulbs at 4100K and three warm white fluorescent bulbs at 3000K per incubator). To induce lipid production, cells were cultured to mid-log phase in regular TAP prior to deprivation of N by transfer to ammonium-free (i.e., nitrogen-free) TAP medium, as described previously. Briefly, cells subjected to nitrogen deprivation were grown to $4 \times 10^6$ cells/mL and collected by centrifugation at 1006×g for 5 min at room temperature. The supernatant was discarded, and the cells were washed in nitrogen-free TAP. Cells were then resuspended in nitrogen-free TAP to a final cell count of $2 \times 10^6$ cells/mL. Cell densities were determined using a hemocytometer.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. A computer-based automated method of sorting particles for flow cytometry, the method comprising: (a) training, by a training device, an artificial neural network (ANN) according to parameters derived from digitally observed features of known particles that belong to at least two known particle classes; (b) tuning, by the training device, weights of the ANN as a function of at least one property of receiver operating characteristics (ROC) curve representing particle classifications of the known particles generated by the ANN based on the digital observed features; (c) configuring a sorting device with the trained and tuned ANN; (d) storing in a computer readable non-transitory memory, by the sorting device, particle sensor data relating to observed particles that are observed by a sensor; (e) converting, by the sorting device, the particle sensor data into digitally observed particle features representing the observed particles; (f) and sorting, by the sorting device, the observed particles into the at least two classes according to the trained and tuned ANN as a function of the observed particle features; (g) wherein said method is performed by executing instructions on a computer processor, and wherein said instructions are stored on a non-transitory memory readable by said computer processor.

2. The method of any preceding embodiment, further comprising heuristically optimizing the weights of the ANN based on sorted observed particles and the observed particle features.

3. The method of any preceding embodiment, wherein the step of heuristically optimizing the weights of the ANN includes calculating new weights via implementations of genetic algorithms that model the weights of the ANN where the new weights are selected based on a fitness value derived from the property of the ROC.

4. The method of any preceding embodiment, wherein the step of optimizing the weights of the ANN is performed by an external device other than the sorting device.

5. The method of any preceding embodiment, wherein the step of tuning the weights of the ANN includes calculating new weights via implementations of genetic algorithms that model the weights of the ANN where the new weights are selected based on a fitness value derived from the property of the ROC.

6. The method of any preceding embodiment, wherein the at least two known particle classes are selected from the group of particle classes consisting of: a true positive class, a false positive class, a true negative class, and a false negative class.

7. The method of any preceding embodiment, wherein the at least two known particle class include at least two of the following: a healthy cell, a diseased cell, a target tissue cell, a type of cancer cell, a circulating tumor cell (CTC), and a blood cell.

8. The method of any preceding embodiment, wherein the step of configuring the storing device with the ANN includes loading the ANN into a non-transitory memory of the sorting device.

9. The method of any preceding embodiment, wherein the step of configuring the storing device with the ANN includes programming a programmable gate array of the sorting device.

10. The method of any preceding embodiment, wherein the programmable gate array includes at least one of the following: a PLA and an FPGA.

11. The method of any preceding embodiment, further comprising measuring at least one of the following ROC curve features as the at least one property: an area under the curve (AUC), maximum distance of the ROC curve from an indifference curve, and a curve slope.

12. The method of any preceding embodiment, wherein the observed features include a measured interference.

13. The method of any preceding embodiment, further comprising generating the ROC curve from the known particle classes or from the observed particles.

14. The method of any preceding embodiment, wherein the observed features include at least one of the following morphology features: a shape, a diameter transverse to flow, a diameter parallel to flow, a perimeter, a circularity, a major axis, an orientation, a loose area, and a median radius.

15. The method of any preceding embodiment, wherein the observed features include at least one of the following optical phase features: an optical path distance with respect to power distribution, an optical path distance with respect to pulse-to-pulse fluctuation, and a refractive index.

16. The method of any preceding embodiment, wherein the observed features include at least one of the following optical loss features: an absorption with respect to power distribution, an absorption with respect to pulse-to-pulse fluctuation, a mean scattering optical loss, and a mean absolute scattering optical loss.

17. The method of any preceding embodiment, wherein the sensor comprises an image sensor.

18. The method of any preceding embodiment, wherein the image sensor comprises a CCD or a CMOS.

19. The method of any preceding embodiment, wherein the observed particles comprise biological cells.

20. The method of any preceding embodiment, wherein the observed particles comprise nanoparticles.

21. The method of any preceding embodiment, wherein the sorting device comprises a flow cytometer.

22. The method of any preceding embodiment, wherein the observed features are derived from time-stretch quantitative phase imaging of the observed particles.

23. The method of any preceding embodiment, wherein the training device and the storing device are included in the same computing device.

24. A particle sorting apparatus, the apparatus comprising: (a) an optical path having a plurality of optical elements toward a particle sorting field of view and characterized as having different path lengths for different wavelengths of light; (b) an optical pulse generator that directs a plurality of optical pulses along the optical path, each pulse comprising multiple wavelengths of light and incident on target particles within the particle sorting field of view; (c) a time-stretch amplifier that converts return optical pulses from the target particles into time-stretched optical pulses according to wavelengths of light in the return optical pulse; (d) an optical sensor that converts the time-stretched optical pulses into a digital interferogram that includes optical phase and information loss associated with at least one of the target particles; (e) a particle feature extractor that extracts particle features from the digital interferogram; and (f) a classification module that classifies the target particles according to known classes defined based on known particle features that are derived based on known optical phase and known information loss, and as a function of the target particle features.

25. The apparatus of any preceding embodiment, wherein the particle features include at least one of the following morphology features derived from the interferogram: a shape, a diameter transverse to flow, a diameter parallel to flow, a perimeter, a circularity, a major axis, an orientation, a loose area, and a median radius.

26. The apparatus of any preceding embodiment, wherein the particle features include at least one of the following optical phase features derived from the interferogram: an optical path distance with respect to power distribution, an optical path distance with respect to pulse-to-pulse fluctuation, and a refractive index.

27. The apparatus of any preceding embodiment, wherein the particle features include at least one of the following optical loss features derived from the interferogram: an absorption with respect to power distribution, an absorption with respect to pulse-to-pulse fluctuation, a mean scattering optical loss, and a mean absolute scattering optical loss.

28. The apparatus of any preceding embodiment, wherein the target particle features further include morphological features of the target cell derived from the interferogram.

29. The apparatus of any preceding embodiment, wherein the optical pulse comprises wavelengths of light in the range from 800 nm to 1700 nm.

30. The apparatus of any preceding embodiment, wherein the optical pulse comprises a duration of no more than 2 ns.

31. The apparatus of any preceding embodiment, wherein the interferogram comprises a duration of no more than 60 ns.

32. The apparatus of any preceding embodiment, wherein the interferogram comprises a duration of no more than 30 ns.

33. The apparatus of any preceding embodiment, wherein the time-stretch amplifier comprises a Raman amplifier coupled with an optical fiber spool.

34. The apparatus of any preceding embodiment, wherein the classification module is coupled with a classification database storing the known particle features correlated with the known classes.

35. The apparatus of any preceding embodiment, wherein the classification module includes a neural network trained according to the known particle features, including the known optical phases and the known information loss of classes of known particles.

36. The apparatus of any preceding embodiment, further comprising an image reconstruction module that reconstructs two-dimensional quantitative optical phase images and loss images from the digital image signal data.

37. The apparatus of any preceding embodiment, wherein the optical phase images and loss images are reconstructed simultaneously from the interferogram.

38. The apparatus of any preceding embodiment, wherein the optical phase images and loss images are reconstructed from serial line images of the at least one target particle.

39. The apparatus of any preceding embodiment, wherein the particle feature extraction module extracts the target particle features from the reconstruction optical phase images and loss images.

40. The apparatus of any preceding embodiment, wherein the target particle comprises a biological tissue.

41. The apparatus of any preceding embodiment, wherein the target particle comprises a biological cell.

42. The apparatus of any preceding embodiment, wherein the biological cell is selected from the group consisting of: a healthy cell, a tumor cell, a blood cell, a liver cell, a pancreatic cell, and a breast cell.

43. The apparatus of any preceding embodiment, further comprising a fluid transport conduit that transports the target particle to a field of view of the image sensor.

44. The apparatus of any preceding embodiment, wherein particle feature extraction module is calibrated according to fluid characteristics of a fluid flowing through the fluid transport conduit.

45. The apparatus as recited in claim 24, wherein the image sensor comprises at least one of the following: a photodetector, a CCD sensor, and a CMOS sensor.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Performance Comparison of Different Classification Algorithms

| Algorithm | Accuracy Avg. Bal. | Accuracy Std. Dev. Bal. | Compute Time (s) |
|---|---|---|---|
| DNN Trained by AUC | 95.5% | 0.9% | 365.6 |
| DNN Trained by Cross Entropy | 94.4% | 2.1% | 4.7 |
| Logistic Regression | 93.5% | 0.9% | 0.8 |
| Support Vector Machine | 93.4% | 1.0% | 1.7 |
| Naïve Bayes | 88.7% | 1.6% | 2.8 |

DNN = Deep Neural Network

TABLE 2A

Performance Comparison of Different Classification Algorithms

| System Category | Component | *Resolvable Points | Lateral Resolution (μm) |
|---|---|---|---|
| Free-Space Optics | Diffraction Gratings | Eq. (11) | 3.09 |
| | Lenses and Mirrors | Eq. (12) | 2.00 |
| Time Stretch | Group Delay Dispersion | Eq. (13) | 0.73 |
| Electronic | Photodetector BW | Eq. (14) | 0.28 |
| Back End | ADC Sampling Rate | Eq. (15) | 0.10 |

*See Table 2B for specific equations

TABLE 2B

Equations for Resolvable Points

| Resolvable Points Eq. # | Number of Resolvable Points |
|---|---|
| Eq. (11) | $N_{grating} = \frac{\Delta\lambda}{\delta\lambda_{grating}} = \frac{\Delta\lambda}{\left(\lambda \cdot \frac{d}{m \cdot 2\omega_0}\right)}$ | where $\Delta\lambda$ is the optical bandwidth, $\lambda$ is the central wavelength, m is the order of diffraction, $\omega_0$ is the beam waist, and d is the groove spacing.

| Eq. (12) | $N_{Abbe} = \frac{FOV}{\delta x_{diffraction}} = \frac{FOV}{\left(\frac{\lambda + \Delta\lambda/2}{2 \cdot NA}\right)}$ | where FOV is the field of view, NA is the numerical aperture of the objective lens.

| Eq. (13) | $N_{DFT} = \frac{\Delta\lambda}{\delta\lambda} = \frac{\Delta\lambda}{\lambda \cdot \sqrt{\frac{2}{DL_f \cdot c}}}$ | where D is the group velocity dispersion, $L_f$ is the dispersive fiber length, and c is speed of light.

| Eq. (14) | $N_{PD} = \frac{\Delta t}{\delta t} = \frac{DL_f \Delta\lambda}{0.35/B}$ | where t is time in frame of optical pulses, D is the group velocity dispersion, $L_f$ is the dispersive fiber length, and B is the bandwidth of the photodetector.

| Eq. (15) | $N_{ADC} = DL_f \Delta\lambda f_{ADC}$ | where D is the group velocity dispersion, $L_f$ is the dispersive fiber length, $f_{ADC}$ is the sampling rate of the digitizer.

What is claimed is:

1. A computer-based automated method of sorting particles for flow cytometry, the method comprising:

training, by a training device, an artificial neural network (ANN) which receives inputs as digitally observed features of known particles that belong to at least two known particle classes;

tuning, by the training device, weights of the ANN as a function of at least one property of receiver operating characteristics (ROC) curve representing particle classifications of the known particles generated by the ANN based on the digitally observed features;

configuring a sorting device with the trained and tuned ANN;

storing in a computer readable non-transitory memory, by the sorting device, particle sensor data relating to observed particles that are observed by a sensor;

converting, by the sorting device, the particle sensor data into digitally observed particle features representing the observed particles; and sorting, by the sorting device, the observed particles into the at least two classes according to the trained and tuned ANN as a function of the observed particle features;

wherein said method is performed by executing instructions on a computer processor, and wherein said instructions are stored on a non-transitory memory readable by said computer processor.

2. The method as recited in claim 1, further comprising heuristically optimizing the weights of the ANN based on sorted observed particles and the observed particle features.

3. The method as recited in claim 2, wherein the step of heuristically optimizing the weights of the ANN includes calculating new weights via implementations of genetic algorithms that model the weights of the ANN where the new weights are selected based on a fitness value derived from the property of the ROC.

4. The method as recited in claim 2, wherein the step of optimizing the weights of the ANN is performed by an external device other than the sorting device.

5. The method as recited in claim 1, wherein the step of tuning the weights of the ANN includes calculating new weights via implementations of genetic algorithms that model the weights of the ANN where the new weights are selected based on a fitness value derived from the property of the ROC.

6. The method as recited in claim 1, wherein the at least two known particle classes are selected from the group of particle classes consisting of: a true positive class, a false positive class, a true negative class, and a false negative class.

7. The method as recited in claim 1, wherein the at least two known particle class include at least two of the following: a healthy cell, a diseased cell, a target tissue cell, a type of cancer cell, a circulating tumor cell (CTC), and a blood cell.

8. The method as recited in claim 1, wherein the step of configuring the storing device with the ANN includes loading the ANN into a non-transitory memory of the sorting device.

9. The method as recited in claim 1, wherein the step of configuring the storing device with the ANN includes programming a programmable gate array of the sorting device.

10. The method as recited in claim 9, wherein the programmable gate array includes at least one of the following: a PLA and an FPGA.

11. The method as recited in claim 1, further comprising measuring at least one of the following ROC curve features as the at least one property: an area under the curve (AUC), maximum distance of the ROC curve from an indifference curve, and a curve slope.

12. The method as recited in claim 1, wherein the observed features include a measured interference.

13. The method as recited in claim 1, further comprising generating the ROC curve from the known particle classes or from the observed particles.

14. The method as recited in claim 1, wherein the observed features include at least one of the following morphology features: a shape, a diameter transverse to flow, a diameter parallel to flow, a perimeter, a circularity, a major axis, an orientation, a loose area, and a median radius.

15. The method as recited in claim 1, wherein the observed features include at least one of the following optical phase features: an optical path distance with respect to power distribution, an optical path distance with respect to pulse-to-pulse fluctuation, and a refractive index.

16. The method as recited in claim 1, wherein the observed features include at least one of the following optical loss features: an absorption with respect to power distribution, an absorption with respect to pulse-to-pulse fluctuation, a mean scattering optical loss, and a mean absolute scattering optical loss.

17. The method as recited in claim 1, wherein the sensor comprises an image sensor.

18. The method as recited in claim 17, wherein the image sensor comprises a CCD or a CMOS.

19. The method as recited in claim 1, wherein the observed particles comprise biological cells.

20. The method as recited in claim 1, wherein the observed particles comprise nanoparticles.

21. The method as recited in claim 1, wherein the sorting device comprises a flow cytometer.

22. The method as recited in claim 1, wherein the observed features are derived from time-stretch quantitative phase imaging of the observed particles.

23. The method as recited in claim 1, wherein the training device and the storing device are included in the same computing device.

* * * * *